(12) United States Patent
Schaeffer et al.

(10) Patent No.: US 9,375,138 B2
(45) Date of Patent: Jun. 28, 2016

(54) STEERABLE GUIDE MEMBER AND CATHETER

(71) Applicants: Darin Schaeffer, Bloomington, IN (US); Patrick Melder, Marietta, GA (US); Vicky Tran, Louisville, KY (US); Logan Cage, Bloomington, IN (US)

(72) Inventors: Darin Schaeffer, Bloomington, IN (US); Patrick Melder, Marietta, GA (US); Vicky Tran, Louisville, KY (US); Logan Cage, Bloomington, IN (US)

(73) Assignee: COOK MEDICAL TECHNOLOGIES LLC, Bloomington, IN (US)

(*) Notice: Subject to any disclaimer, the term of this patent is extended or adjusted under 35 U.S.C. 154(b) by 361 days.

(21) Appl. No.: 13/684,148

(22) Filed: Nov. 21, 2012

(65) Prior Publication Data

US 2013/0137920 A1   May 30, 2013

Related U.S. Application Data

(60) Provisional application No. 61/563,653, filed on Nov. 25, 2011.

(51) Int. Cl.
| | | |
|---|---|---|
| A61B 1/00 | (2006.01) | |
| A61B 1/07 | (2006.01) | |
| A61B 1/04 | (2006.01) | |
| A61B 17/24 | (2006.01) | |
| A61B 1/233 | (2006.01) | |
| G02B 23/24 | (2006.01) | |
| G02B 23/26 | (2006.01) | |
| A61M 25/01 | (2006.01) | |
| A61M 25/06 | (2006.01) | |

(Continued)

(52) U.S. Cl.
CPC ............... *A61B 1/07* (2013.01); *A61B 1/00082* (2013.01); *A61B 1/00154* (2013.01); *A61B 1/04* (2013.01); *A61B 1/233* (2013.01); *A61B 17/24* (2013.01); *G02B 23/2469* (2013.01); *G02B 23/2476* (2013.01); *G02B 23/26* (2013.01); *A61M 25/01* (2013.01); *A61M 25/0662* (2013.01); *A61M 25/1002* (2013.01); *A61M 25/1011* (2013.01); *A61M 2025/105* (2013.01); *G02B 6/0008* (2013.01)

(58) Field of Classification Search
USPC ......... 600/121–123, 128–129, 136, 138–142; 604/95.04, 528
See application file for complete search history.

(56) References Cited

U.S. PATENT DOCUMENTS

| | | | |
|---|---|---|---|
| 3,081,767 | A | 3/1963 | Hett |
| 3,521,620 | A | 7/1970 | Cook |

(Continued)

FOREIGN PATENT DOCUMENTS

| | | |
|---|---|---|
| EP | 0163266 | 12/1985 |
| EP | 2522386 | 11/2012 |

(Continued)

OTHER PUBLICATIONS

European Patent Office, European Search Report for application No. 12194127.2 mailed Apr. 9, 2013, p. 1-5.

(Continued)

*Primary Examiner* — Matthew J Kasztejna
*Assistant Examiner* — Rynae Boler
(74) *Attorney, Agent, or Firm* — Buchanan Nipper

(57) ABSTRACT

Medical devices are described and illustrated herein. In particular, steerable guide members and catheters useful in the identification and treatment of bodily passages are provided. Methods of identifying and treating bodily passages are also provided.

4 Claims, 10 Drawing Sheets

(51) Int. Cl.
  *A61M 25/10* (2013.01)
  *F21V 8/00* (2006.01)

(56) References Cited

U.S. PATENT DOCUMENTS

| | | | |
|---|---|---|---|
| 3,625,200 A | 12/1971 | Muller | |
| 4,474,174 A * | 10/1984 | Petruzzi | 600/104 |
| 4,696,544 A * | 9/1987 | Costella | 600/114 |
| 4,719,924 A | 1/1988 | Crittenden et al. | |
| 4,826,087 A | 5/1989 | Chinery | |
| 4,841,976 A | 6/1989 | Packard et al. | |
| 4,886,067 A | 12/1989 | Palermo | |
| 5,176,126 A * | 1/1993 | Chikama | 600/139 |
| 5,447,503 A | 9/1995 | Miller | |
| 5,470,330 A | 11/1995 | Goldenberg et al. | |
| 5,480,382 A | 1/1996 | Hammerslag et al. | |
| 5,643,251 A * | 7/1997 | Hillsman et al. | 606/7 |
| 5,674,197 A | 10/1997 | van Muiden et al. | |
| 5,820,546 A * | 10/1998 | Ouchi | 600/123 |
| 5,931,811 A | 8/1999 | Haissaguerre et al. | |
| 6,027,460 A * | 2/2000 | Shturman | 600/129 |
| 6,033,378 A | 3/2000 | Lundquist et al. | |
| 6,066,125 A | 5/2000 | Webster, Jr. | |
| 6,096,036 A | 8/2000 | Bowe et al. | |
| 6,123,699 A | 9/2000 | Webster, Jr. | |
| 6,126,649 A | 10/2000 | VanTassel et al. | |
| 6,183,463 B1 | 2/2001 | Webster, Jr. | |
| 6,206,870 B1 | 3/2001 | Kanner | |
| 6,226,432 B1 | 5/2001 | Gonda et al. | |
| 6,261,284 B1 * | 7/2001 | Ouchi | 600/121 |
| 6,500,167 B1 | 12/2002 | Webster, Jr. | |
| 6,814,697 B2 * | 11/2004 | Ouchi | 600/121 |
| 6,829,497 B2 | 12/2004 | Mogul | |
| 7,056,314 B1 | 6/2006 | Florio et al. | |
| 7,198,599 B2 * | 4/2007 | Goto et al. | 600/154 |
| 7,273,468 B2 | 9/2007 | Bedell | |
| 7,351,214 B2 | 4/2008 | Burgermeister | |
| 7,361,168 B2 | 4/2008 | Makower et al. | |
| 7,410,480 B2 | 8/2008 | Muni et al. | |
| 7,462,175 B2 | 12/2008 | Chang et al. | |
| 7,500,971 B2 | 3/2009 | Chang et al. | |
| 7,520,876 B2 | 4/2009 | Ressemann et al. | |
| 7,559,925 B2 | 7/2009 | Goldfarb et al. | |
| 7,645,272 B2 | 1/2010 | Chang et al. | |
| 7,654,997 B2 | 2/2010 | Makower et al. | |
| 7,658,305 B2 | 2/2010 | Voegele et al. | |
| 7,678,099 B2 | 3/2010 | Ressemann et al. | |
| 7,691,095 B2 | 4/2010 | Bednarek et al. | |
| 7,717,933 B2 | 5/2010 | Becker | |
| 7,720,521 B2 | 5/2010 | Chang et al. | |
| 7,727,186 B2 | 6/2010 | Makower et al. | |
| 7,727,226 B2 | 6/2010 | Chang et al. | |
| 7,740,642 B2 | 6/2010 | Becker | |
| 7,753,929 B2 | 7/2010 | Becker | |
| 7,753,930 B2 | 7/2010 | Becker | |
| 7,771,409 B2 | 8/2010 | Chang et al. | |
| 7,785,252 B2 | 8/2010 | Danitz et al. | |
| 7,803,150 B2 | 9/2010 | Chang et al. | |
| 7,811,277 B2 | 10/2010 | Boulais | |
| 7,854,744 B2 | 12/2010 | Becker | |
| 7,867,218 B1 | 1/2011 | Voda | |
| 7,879,061 B2 | 2/2011 | Keith et al. | |
| 7,892,233 B2 | 2/2011 | Hall et al. | |
| 7,918,871 B2 | 4/2011 | Truitt et al. | |
| 7,959,601 B2 | 6/2011 | McDaniel et al. | |
| 8,029,461 B2 | 10/2011 | Thielen et al. | |
| 8,066,664 B2 | 11/2011 | LaDuca et al. | |
| 8,083,879 B2 | 12/2011 | Swinehart et al. | |
| 8,088,101 B2 | 1/2012 | Chang et al. | |
| 8,090,433 B2 * | 1/2012 | Makower et al. | 600/510 |
| 8,100,933 B2 | 1/2012 | Becker | |
| 8,114,062 B2 | 2/2012 | Muni et al. | |
| 8,123,722 B2 | 2/2012 | Chang et al. | |
| 8,142,422 B2 | 3/2012 | Makower et al. | |
| 8,216,210 B2 | 7/2012 | Ostrovsky et al. | |
| 8,241,266 B2 | 8/2012 | Keith et al. | |
| 8,277,478 B2 | 10/2012 | Drontle et al. | |
| 8,282,667 B2 | 10/2012 | Drontle et al. | |
| 8,317,816 B2 | 11/2012 | Becker | |
| 8,388,642 B2 | 3/2013 | Muni et al. | |
| 8,414,473 B2 | 4/2013 | Jenkins et al. | |
| 8,425,457 B2 | 4/2013 | John et al. | |
| 8,435,290 B2 | 5/2013 | Clifford et al. | |
| 2003/0216711 A1 | 11/2003 | Rabiner et al. | |
| 2004/0019252 A1 * | 1/2004 | Hirata | 600/114 |
| 2005/0038412 A1 | 2/2005 | Rabiner et al. | |
| 2005/0159728 A1 | 7/2005 | Armour et al. | |
| 2006/0149129 A1 * | 7/2006 | Watts et al. | 600/113 |
| 2006/0252993 A1 * | 11/2006 | Freed et al. | 600/146 |
| 2007/0129751 A1 | 6/2007 | Muni et al. | |
| 2007/0167682 A1 * | 7/2007 | Goldfarb et al. | 600/114 |
| 2007/0208252 A1 | 9/2007 | Makower | |
| 2007/0282305 A1 | 12/2007 | Goldfarb et al. | |
| 2007/0293727 A1 | 12/2007 | Goldfarb et al. | |
| 2008/0015472 A1 | 1/2008 | Ressemann et al. | |
| 2008/0015544 A1 | 1/2008 | Keith et al. | |
| 2008/0103521 A1 | 5/2008 | Makower et al. | |
| 2008/0119693 A1 | 5/2008 | Makower et al. | |
| 2008/0132938 A1 | 6/2008 | Chang et al. | |
| 2008/0172033 A1 | 7/2008 | Keith et al. | |
| 2008/0195041 A1 | 8/2008 | Goldfarb et al. | |
| 2008/0228085 A1 | 9/2008 | Jenkins et al. | |
| 2008/0275483 A1 | 11/2008 | Makower et al. | |
| 2008/0287908 A1 | 11/2008 | Muni et al. | |
| 2008/0287918 A1 | 11/2008 | Rosenman et al. | |
| 2008/0319424 A1 | 12/2008 | Muni et al. | |
| 2009/0030274 A1 | 1/2009 | Goldfarb et al. | |
| 2009/0187098 A1 | 7/2009 | Makower et al. | |
| 2009/0198216 A1 | 8/2009 | Muni et al. | |
| 2009/0216196 A1 | 8/2009 | Drontle et al. | |
| 2009/0240112 A1 | 9/2009 | Goldfarb et al. | |
| 2009/0240237 A1 | 9/2009 | Goldfarb et al. | |
| 2009/0312745 A1 | 12/2009 | Goldfarb et al. | |
| 2009/0326450 A1 | 12/2009 | Ostrovsky et al. | |
| 2010/0030113 A1 | 2/2010 | Morriss et al. | |
| 2010/0042046 A1 | 2/2010 | Chang et al. | |
| 2010/0076269 A1 | 3/2010 | Makower et al. | |
| 2010/0106141 A1 | 4/2010 | Osypka et al. | |
| 2010/0114066 A1 | 5/2010 | Makower et al. | |
| 2010/0168511 A1 | 7/2010 | Muni et al. | |
| 2010/0174138 A1 | 7/2010 | Chang et al. | |
| 2010/0174308 A1 | 7/2010 | Chang et al. | |
| 2010/0198191 A1 | 8/2010 | Clifford et al. | |
| 2010/0198247 A1 | 8/2010 | Chang et al. | |
| 2010/0211007 A1 | 8/2010 | Lesch, Jr. et al. | |
| 2010/0217261 A1 | 8/2010 | Watson | |
| 2010/0262075 A1 | 10/2010 | Danitz et al. | |
| 2010/0268087 A1 | 10/2010 | Hirota | |
| 2010/0268245 A1 | 10/2010 | Chang et al. | |
| 2010/0274188 A1 | 10/2010 | Chang et al. | |
| 2010/0298862 A1 | 11/2010 | Chang et al. | |
| 2010/0331776 A1 | 12/2010 | Salahieh et al. | |
| 2011/0004057 A1 | 1/2011 | Goldfarb et al. | |
| 2011/0009700 A1 | 1/2011 | Ostrovsky et al. | |
| 2011/0060214 A1 | 3/2011 | Makower | |
| 2011/0071349 A1 | 3/2011 | Drontle et al. | |
| 2011/0112476 A1 | 5/2011 | Kauphusman et al. | |
| 2011/0112512 A1 | 5/2011 | Muni et al. | |
| 2011/0160740 A1 | 6/2011 | Makower et al. | |
| 2011/0190831 A1 | 8/2011 | Mafi et al. | |
| 2011/0218492 A1 | 9/2011 | McDaniel et al. | |
| 2011/0224652 A1 | 9/2011 | Drontle et al. | |
| 2011/0288477 A1 | 11/2011 | Ressemann et al. | |
| 2011/0313392 A1 | 12/2011 | Varghese et al. | |
| 2012/0010646 A1 | 1/2012 | Keith et al. | |
| 2012/0071824 A1 | 3/2012 | Chang et al. | |
| 2012/0101441 A1 | 4/2012 | Sargent, Jr. | |
| 2012/0116254 A1 | 5/2012 | Morriss | |
| 2012/0136207 A1 | 5/2012 | Goldfarb et al. | |
| 2012/0172912 A1 | 7/2012 | Ressemann et al. | |
| 2012/0184983 A1 | 7/2012 | Chang et al. | |
| 2012/0190973 A1 | 7/2012 | Ressemann et al. | |
| 2012/0238952 A1 | 9/2012 | Mitchell et al. | |
| 2012/0245419 A1 | 9/2012 | Makower et al. | |

(56) References Cited

U.S. PATENT DOCUMENTS

| | | |
|---|---|---|
| 2012/0265094 A1 | 10/2012 | Goldfarb et al. |
| 2012/0283625 A1 | 11/2012 | Keith et al. |
| 2013/0096605 A1 | 4/2013 | Becker |

FOREIGN PATENT DOCUMENTS

| | | |
|---|---|---|
| WO | WO2006020180 | 2/2006 |
| WO | WO2008045242 | 4/2008 |
| WO | WO2011082074 | 7/2011 |
| WO | WO2011084655 | 7/2011 |

OTHER PUBLICATIONS

European Patent Office, European Extended Search Report for application No. 12194127.2 mailed Jul. 25, 2013, p. 1-8.

* cited by examiner

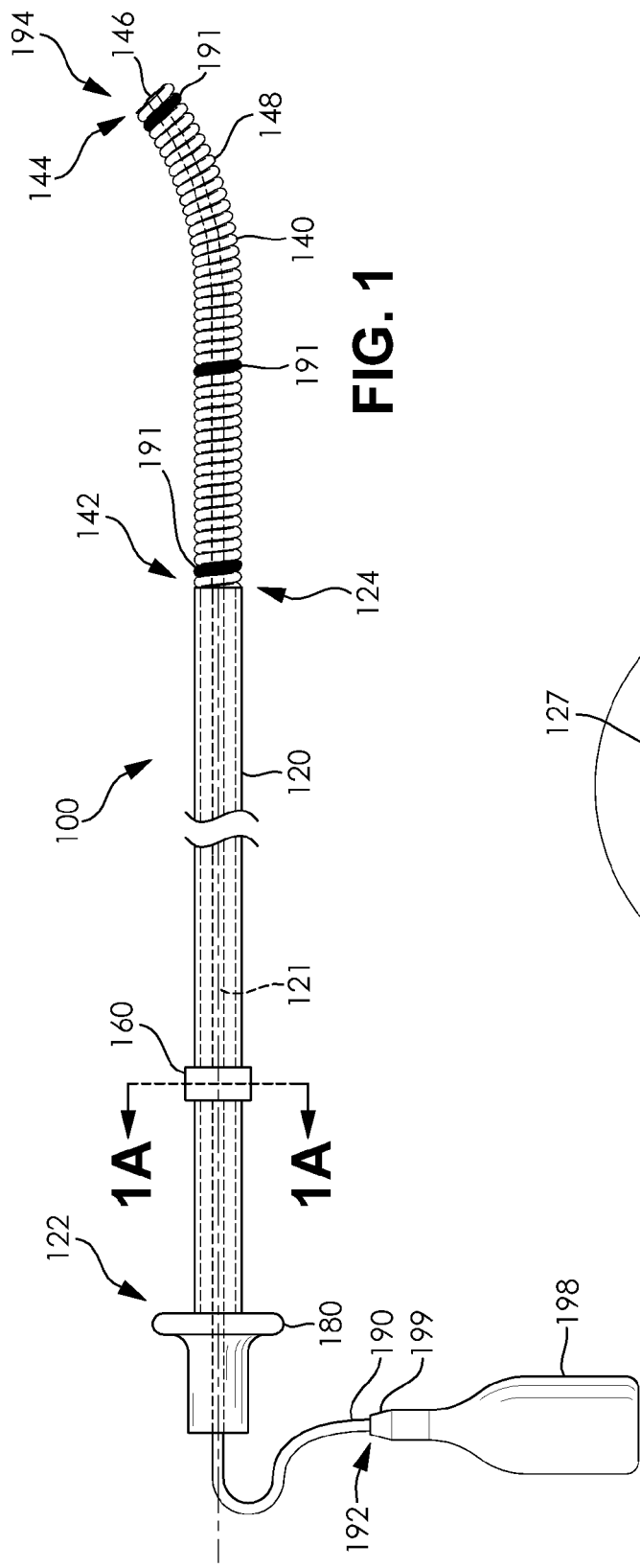
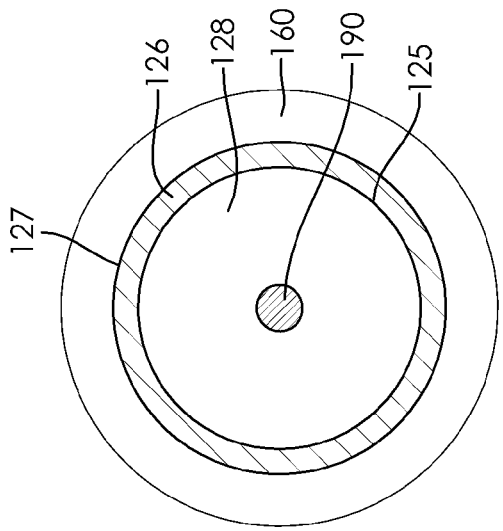
FIG. 1
FIG. 1A

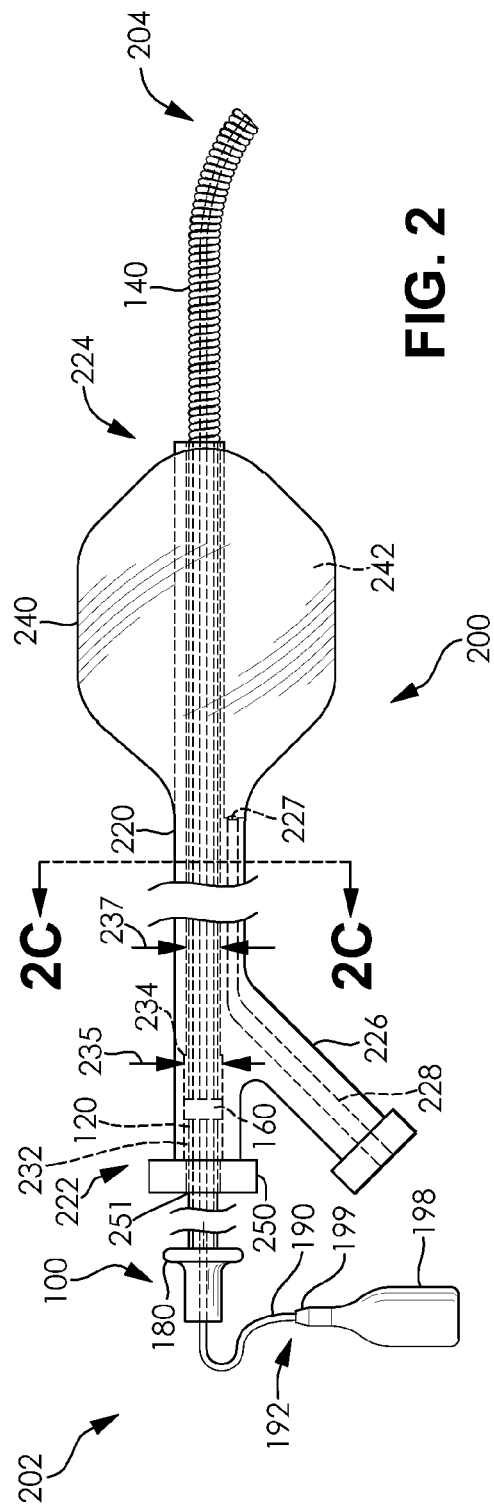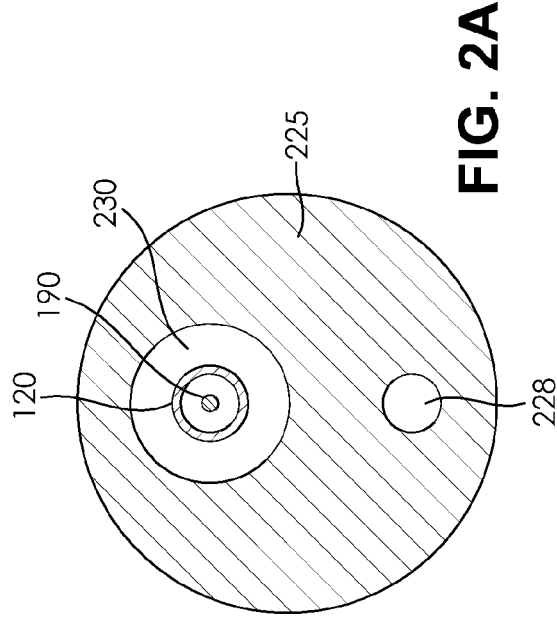

STEERABLE GUIDE MEMBER AND CATHETER

FIELD

The invention relates generally to the field of medical devices. More particularly, the invention relates to steerable guide members and catheters useful in the identification and treatment of bodily passages.

BACKGROUND

It is sometimes necessary or otherwise desirable to treat bodily passages using a balloon catheter. For example, when sinus cavities become blocked, balloon sinuplasty, the dilation of the sinus using a balloon catheter, provides an alternative to radical surgical approaches to unblocking the sinus.

Conventional sinuplasty procedures place a balloon catheter over a previously placed wireguide and are complicated by the need to use x-ray or other visualization equipment to verify positioning of the balloon and wireguide in the proper sinus cavity prior to the actual dilation procedure. Lighted wireguides have been developed to facilitate the visualization process, but still present significant drawbacks. For example, lighted wireguides cannot be torqued because they typically include a coil that extends the entire length of the wireguide and lack a rigid inner member. As a result, these devices are not steerable, which limits the ability of a user to navigate the device towards a point of treatment.

In addition, with respect to treating an airway, such as the trachea, a user generally advances a balloon catheter freely towards a point of treatment beyond the vocal chords. These devices do not allow a user to steer the distal end of the catheter through the anatomy of a patient. Therefore, to complete treatment, a user continuously advances and withdraws the distal end of the catheter from a portion of the airway to navigate past the vocal chords. As a result, the complexity and the length of time the procedure takes to complete are increased.

Therefore, a need exists for steerable guide members and catheters assemblies that include such guide members.

SUMMARY

Several exemplary guide members and medical devices are described herein. For example, several exemplary guide members and medical devices adapted to be used with a light source and/or camera for the identification and treatment of bodily passages are described herein.

An exemplary guide member that is adapted to be used with a light source for the identification and treatment of a bodily passage comprises an elongate tubular member, a coil member, and an optical fiber. The elongate tubular member has a first proximal end and a first distal end, and defines a first lumen that extends between the first proximal end and the first distal end. The coil member has a second proximal end and a second distal end, and defines a second lumen that extends between the second proximal end and the second distal end. The second proximal end of the coil member is attached to the first distal end of the elongate tubular member. The optical fiber is disposed in the first lumen of the elongate tubular member and the second lumen of the coil member. The optical fiber has a third proximal end that is adapted to be operatively connected to the light source and a third distal end that is attached to the coil member. The coil member is flexible and is adapted to define a curve that is disposed between the second proximal end and the second distal end.

An exemplary medical device that is adapted to be used with a light source for the identification and treatment of a bodily passage comprises a catheter and a guide member. The catheter comprises an elongate main body and a balloon attached to the elongate main body. The elongate main body has a first proximal end and a first distal end and defines a first lumen. The balloon is adapted to move between a deflated configuration and an inflated configuration. The guide member is disposed within the first lumen of the elongate main body and comprises an elongate tubular member, a coil member, and an optical fiber. The elongate tubular member has a second proximal end and a second distal end, and defines a second lumen that extends between the second proximal end and the second distal end. The coil member has a third proximal end and a third distal end, and defines a third lumen that extends between the third proximal end and the third distal end. The third proximal end of the coil member is attached to the second distal end of the elongate tubular member. The optical fiber is disposed in the second lumen of the elongate tubular member and the third lumen of the coil member. The optical fiber has a fourth proximal end that is adapted to be operatively connected to the light source and a fourth distal end that is attached to the coil member. The coil member is flexible and adapted to define a curve disposed between the second proximal end and the second distal end.

Another exemplary medical device that is adapted to be used with a light source for the identification and treatment of a bodily passage comprises a catheter and a guide member. The catheter comprises an elongate main body and a balloon attached to the elongate main body. The elongate main body has a first proximal end and a first distal end and defines a first lumen. The balloon is adapted to move between a deflated configuration and an inflated configuration. The guide member is disposed within the first lumen of the elongate main body and comprises an elongate tubular member, a fitting, a coil member, and an optical fiber. The elongate tubular member has a second proximal end and a second distal end, and defines a second lumen that extends between the second proximal end and the second distal end. The fitting is releasably attached to the elongate tubular member and extends radially outward from the elongate tubular member. The coil member has a third proximal end and a third distal end, and defines a third lumen that extends between the third proximal end and the third distal end. The third proximal end of the coil member is attached to the second distal end of the elongate tubular member. The optical fiber is disposed in the second lumen of the elongate tubular member and the third lumen of the coil member. The optical fiber has a fourth proximal end that is adapted to be operatively connected to the light source and a fourth distal end that is attached to the coil member. A portion of the optical fiber is attached to the elongate tubular member. The coil member is flexible and adapted to define a curve disposed between the second proximal end and the second distal end. The guide member is movable within the first lumen between a first position and a second position. In the first position, the third distal end of the coil member is disposed in a first coil position relative to the first distal end of the elongate main body. In the second position, the third distal end of the coil member is disposed in a second coil position relative to the first distal end of the elongate main body.

In addition, several exemplary methods of identifying and treating bodily passages are described herein. For example several exemplary methods using exemplary guide members and/or medical device are provided.

Additional understanding of the devices and methods contemplated and/or claimed by the inventors can be gained by reviewing the detailed description of exemplary embodiments, presented below, and the referenced drawings.

BRIEF DESCRIPTION OF THE DRAWINGS

FIG. 1 is a side view of an exemplary guide member.
FIG. 1A is a sectional view of the guide member illustrated in FIG. 1, taken along line 1A-1A in FIG. 1.
FIG. 2 is a side view of an exemplary catheter disposed over the guide member illustrated in FIG. 1.
FIG. 2A is a sectional view of the catheter illustrated in FIG. 2, taken along line 2A-2A in FIG. 2.

DETAILED DESCRIPTION

Figure 3:
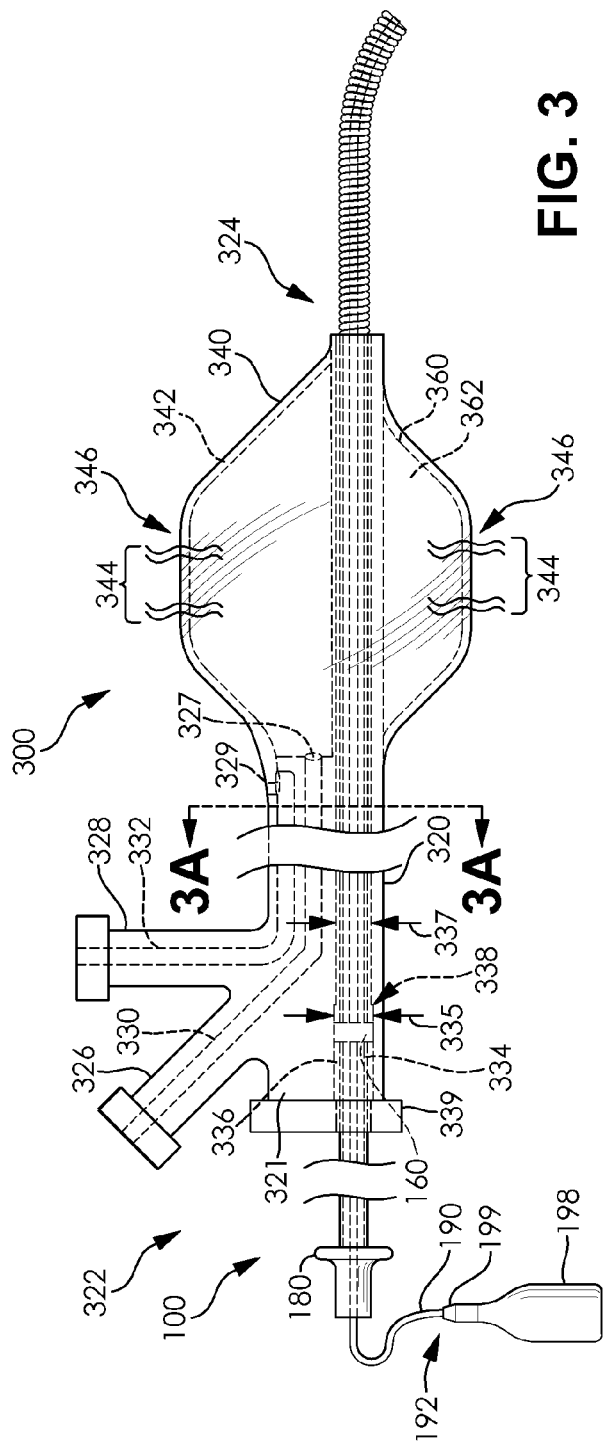
FIG. 3 is a side view of another exemplary catheter disposed over the guide member illustrated in FIG. 1.

The following description of exemplary embodiments provides illustrative examples of that which the inventors regard as their invention. As such, the embodiments discussed herein are merely exemplary in nature and are not intended to limit the scope of the invention, or its protection, in any manner. Rather, the description of these exemplary embodiments serves to enable a person of ordinary skill in the relevant art to practice the invention.

As used herein, the term "bodily passage" refers to any passage within the body of an animal, including, but not limited to, humans, and includes elongate passages. The term "sinus passage" refers to the nasal passages and includes, but is not limited to, eustachian tube(s), primary ostium, and/or accessory ostium. The term "airway" refers to any airway including, but not limited to, the nasopharynx, oropharynx, pharynx, trachea, bronchial tubes, esophagus, and/or lungs. The term "sinus cavity" refers to the frontal, ethmoid, sphenoid, and/or maxillary sinus. The term "damage" refers to shattering, cracking, breaking, fracturing, fragmenting, puncturing, penetrating, ripping, tearing, dilating, and/or perforating. The term "attached" refers to the fixed, releasable, or integrated association of two or more elements and/or devices. Thus, the term "attached" includes releasably attaching or fixedly attaching two or more elements. The term "medication" refers to any fluid, drug, and/or agent used to treat a patient.

FIGS. 1 and 1A illustrate an exemplary guide member 100 comprising an elongate tubular member 120, coil member 140, projection 160, fitting 180, and an optical fiber 190.

The elongate tubular member 120 comprises a lengthwise axis 121 extending through its length, a proximal end 122, a distal end 124, and a wall 126. The wall 126 has an interior surface 125, an exterior surface 127, and defines a lumen 128 that extends between openings at the proximal end 122 and distal end 124. The elongate tubular member 120 is formed of a rigid material such as nickel titanium, however, other materials, including semi-rigid materials, are considered suitable, and skilled artisans will be able to select an appropriate material according to a particular embodiment base on various considerations, such as the procedure being performed, among others. Examples of materials considered suitable include, but are not limited to, biocompatible materials, stainless steel, and the like.

The coil member 140 comprises a proximal end 142, distal end 144, lumen 146, and curve 148. The coil member 140 defines lumen 146 between openings at the proximal end 142 and the distal end 144. The coil member 140 is formed of a flexible material and is adapted to define curve 148 between the proximal end 142 and the distal end 144. A skilled artisan will be able to select a suitable material for a coil member according to a particular embodiment based on various considerations, such as the intended use of the device. An example material considered suitable to form a coil member includes, but is not limited to, biocompatible materials, nickel titanium, stainless steel, and the like.

Curve 148 can be formed in the coil member 140 using various techniques (e.g., by pulling the coil over a blunt object), and skilled artisans will be able to select an appropriate method for forming the curve according to a particular embodiment based on various considerations, such as the type of procedure to be completed, among others.

The proximal end 142 of coil member 140 is attached to the distal end 124 of the elongate tubular member 120. Attachment between the proximal end 142 of the coil member 140 and the distal end 124 of the elongate tubular member 120 can be accomplished using a variety of techniques, and skilled artisans will be able to select an appropriate technique according to a particular embodiment based on various considerations, such as the configuration of the distal end 124 of the elongate tubular member 120, and/or the configuration of the proximal end 142 of the coil member 140, among others. Examples of suitable methods of attaching the coil member 140 to the elongate tubular member 120 include, but are not limited to, fusing, welding, adhering, and/or soldering the proximal end 142 of the coil member 140 to the distal end 124 of the elongate tubular member 120.

While the proximal end 142 of the coil member 140 has been described as attached to the distal end 124 of the elongate tubular member 120, the distal end 124 of the elongate tubular member 120 and/or the proximal end 142 of the coil member 140 can have any suitable structural arrangement to accomplished attachment between the elongate tubular member 120 and coil member 140. A skilled artisan will be able to select a suitable configuration according to a particular embodiment based on various considerations, including the intended use of the device. Example structural arrangements considered suitable include, but are not limited to, using a butt joint, extending a coil radially outward such that a distal end of an elongate tubular member can be introduced into a lumen of the coil member, and/or providing an elongate tubular member with a distal end that defines a taper such that the distal end of the elongate tubular member can be introduced into a lumen of a coil member.

Optionally, a lubricious coating can be included along a portion, or the entirety, of the length of the elongate tubular member 120 and/or the coil member 140. Any suitable lubricious coating can be used, and skilled artisans will be able to select a suitable lubricious coating according to a particular embodiment based on various considerations, such as the bodily passage within which the device is intended to be used. Examples of lubricious coatings considered suitable include, but are not limited to, polymers such as polytetrafluoroethylene (PTFE), and any other polymer or substance having properties that result in the lowering of the coefficient of friction between the outer surface of the elongate tubular member 120 and/or the coil member 140 and the surface in which the outer surface of the elongate tubular member 120 and/or coil member 140 is intended to, or may, contact.

Various alternative structural arrangements of the coil member 140 are considered suitable for inclusion with a guide member 100. For example, the curve 148 of the coil member 140 can be omitted, or multiple curves can be incorporated into, and defined by, the coil member 140. In addition, alternative to attaching a coil member 140 to the distal end 124 of an elongate tubular member 120, which can be formed of the same, or different material as the coil member 140, the distal end of the elongate tubular member can be laser cut into a spiral configuration to provide a guide member 100 with a flexible distal end. In this configuration, the elongate tubular member and the coil member can be formed of the same material.

Projection 160 is disposed on the exterior surface 127 of the wall 126 of the elongate tubular member 120 between the proximal end 122 and the distal end 124 of the elongate tubular member 120. The projection 160 extends radially outward from the elongate tubular member 120 and can be fixedly attached, removably attached, integral with, or separate from the elongate tubular member 120. Projection 160 extends circumferentially about the entirety of the elongate tubular member 120, however, other configurations are considered suitable. For example, the projection 160 can circumferentially extend around a portion of the elongate tubular member 120. Projection 160 advantageously provides a mechanical stop for limiting proximal and distal progression of the guide member 100 when used in combination with a catheter, as described in more detail below. Alternatively, projection 160 can be omitted to allow a device to be advanced over a length of the guide member 100.

While the elongate tubular member 120 and the projection 160 have been described as being circular in nature, other configurations are considered suitable, and skilled artisans will be able to select an appropriate configuration according to a particular embodiment based on various considerations, such as the configuration of the recess 232 and guide member lumen 230 of the main body 220 of the catheter 200, among others.

Fitting 180 is disposed on the proximal end 124 of the elongate tubular member 120 and extends radially outward from the elongate tubular member 120. Fitting 180 can be fixedly attached, removably attached, integral with, or separate from the elongate tubular member 120. Fitting 180 is configured to communicate torque to the attached elongate tubular member 120 and coil member 140 when the user rotates the fitting 180. The fitting 180 can have any suitable configuration, and skilled artisans will be able to select an appropriate configuration for a particular embodiment based on various considerations, such as the amount of torque to be communicated to the coil member 140, among others. For example, the fitting 180 can circumferentially extend about the entirety of, or a portion of, the elongate tubular member 120. In addition, when fitting 180 is releasably attached to the fitting 180 any suitable method of attachment can be utilized, and skilled artisans will be able to select a suitable means for attachment based on various considerations, such as the intended use of the device. Examples methods considered suitable include, but are not limited to, using threaded components, snap fit, or otherwise. Alternatively, the fitting can be omitted from the guide member.

Optical fiber 190 extends between a proximal end 192 and a distal end 194 and defines a light path extending through its length. The optical fiber 190 is disposed within, and extends through, the lumen 128 of the elongate tubular member 120 (e.g., first optic lumen), and the lumen 146 of coil member 140 (e.g., second optic lumen). The proximal end 192 of the optical fiber is adapted to be operatively connected, and/or attached, to a light source 198. The distal end 194 of the optical fiber 190 is attached to the coil member 140. The optical fiber 190 can be attached to the interior surface 125 of the wall 126 of the elongate tubular member 120, and/or the coil member 140, at a variety of locations along the length of these components. For example, the optical fiber 190 can be attached along the entire length, or at one or more locations along the length, of the elongate tubular member 120 and/or the coil member 140, such as at locations 191.

Attaching the optical fiber 190, or a portion thereof, at one or more locations along the length of the elongate tubular member 120 and/or coil member 140 is considered advantageous at least because it increases the torquability of the guide member 100 while maintaining flexibility of the coil member 140. For example, a portion of the optical fiber 190 can be attached at the distal end 124 of the elongate tubular member 120 and another portion of the optical fiber 190 can be attached at the distal end 144 of the coil member 140. Attachment of the optical fiber 190 to the elongate tubular member 120 and/or coil member 140 can be accomplished using any suitable method of attachment, and skilled artisans will be able to select a suitable method of attachment based on various considerations, such as the intended use of the device. An example of a suitable method of attachment includes, but is not limited to, using an adhesive, fusing, and/or welding.

The optical fiber 190 can be configured to emit light axially and/or radially. For example, axially-directed light can be emitted distally from the distal end 194 of the optical fiber 190, while radially-directed light can be emitted radially by the optical fiber 190 distal to, or within, coil member 140 and/or elongate tubular member 120. While the optical fiber 190 has been described and illustrated as attached to the coil member 140, the optical fiber 190 can, alternatively, be omitted from the guide member 100 and provided separately.

Attaching the optical fiber 190 to the coil member 140 and/or elongate tubular member 120 can be accomplished using various methods, materials, and at various times during assembly of the guide member 100. For example, the optical fiber 190 can be inserted through the lumen 128 of the elongate tubular member 120 and lumen 146 of the coil member 140 before, during, or after the coil member 140 has been attached to the elongate tubular member 120. The distal end 194 of the optical fiber 190 can then be trimmed accordingly. In an example where the coil member 140 is adhesively attached to the elongate tubular member 120, the optical fiber 190 can be inserted into the lumen 128 of the elongate tubular member 120 and the lumen 146 of the coil member 140 prior to joining the coil member 140 to the elongate tubular member 120, which assists in attaching the coil member 140 to the elongate tubular member 120.

Any suitable optical fiber 190 can be used in the guide member 100. Commercially available optical fibers considered suitable for use in the guide members described herein include plastic optical fibers and glass optical fibers, with or without cladding. The optical fiber 190 can have any suitable length, and skilled artisans will be able to select an appropriate length for inclusion in a guide member according to a particular embodiment based on various considerations, such as the intended use of the guide member, among others. For example, the optical fiber 190 can be trimmed flush with, proximal to, or distal to the distal end 144 of the coil member 140. The optical fiber 190 can include a length that allows a portion of the optical fiber to extend proximal to the proximal end 122 of the elongate tubular member 120 to the light source 198. When the optical fiber 190 extends proximal to the proximal end 122 of the elongate tubular member 120 an extension sheath (not shown) can be disposed over the optical fiber 190 from the proximal end of the elongate tubular member to the light source 198.

Optionally, the optical fiber 190 can define a curve between its proximal end 192 and the distal end 194. The curve can be formed using various techniques, and skilled artisans will be able to select an appropriate method for forming a curve in a optical fiber according to a particular embodiment based on various considerations, such as the type optical fiber being used. An example technique considered suitable to form a curve in a optical fiber 190 includes, but is not limited to, heating a portion of the optical fiber 190 as it is maintained in a curved shape to incorporate memory of the curve into the optical fiber 190.

The light source 198 is operatively attached to the proximal end 192 of the optical fiber 190 and includes a fiber coupling 199 which provides communication between the light source 198 and the optical fiber 190. Light generated by the light source 198 travels through the light path defined by the optical fiber 190 and is emitted axially, and/or radially, from the optical fiber 190. Alternatively, the proximal end 122 of the elongate tubular member 120 can include one or more connectors for attaching the light source 198 to the elongate tubular member 120. The light source 198 can include one or more switches to allow a user to selectively turn on and off, or dim, optical fiber 190. While the light source 198 has been described and illustrated as attached to the proximal end 192 of the optical fiber 190, the light source 198 can, alternatively, be omitted from the guide member 100 and provided separately.

Any suitable light source 198 can be used with the guide member 100. Commercially-available light sources considered suitable for use with the guide member 100 include xenon, laser, LED, halogen, and other suitable light sources. While particular light sources have been described, skilled artisans will be able to select an appropriate light source for inclusion in a guide member according to a particular embodiment based on various considerations, including the location of the bodily passage being identified and/or treated, among others.

It is noted that, while a single optical fiber 190 is described and illustrated, two or more optical fibers can be used to independently to provide axially-directed and/or radially-directed light. The two or more optical fibers can each extend through the lumen 126 of the elongate tubular member 120 and the lumen 146 of the coil member 140 and can be operatively attached to the same light source, or two separate light sources. Optionally, the two or more optical fibers can be omitted from the guide member 100 and provided separately.

Alternatively, the optical fiber can comprise two separate lengths, a first length disposed in the lumen 128 of the elongate tubular member 120 extending between the proximal end 122 and the distal end 146 of the coil member 140 and a second length extending from the fitting 180 to the light source 198. In this embodiment, the fitting 180 includes any suitable method of attaching the first length and the second length to one another such that light can travel between a light path defined by the first length and a light path defined by the second length. A skilled artisan will be able to select a suitable method for attaching the first length to the second length according to a particular embodiment based on various considerations, such as the intended use of the device. An example of a suitable method of attaching the first length to the second length includes, but is not limited to, using a optical fiber coupling.

In this embodiment, the fitting 180 is releasably attached to the proximal end 122 of the elongate tubular member 120 and projection 160 is omitted to allow any suitable medical device to be advanced over the guide member 100. A skilled artisan will be able to select any suitable medical device to use in combination with a guide member according to a particular embodiment based on various considerations, such as the intended use of the device. Example devices considered suitable to advance over a length of an elongate tubular member include, but are not limited to, catheters, irrigation catheters, balloon catheters, and any other suitable medical device.

Alternative to, or in addition to, the use of an optical fiber 190, the guide member 100 can optionally include a camera disposed on the distal end of the coil member 140 configured to transmit images to a display for a user to determine the location of the distal end of the guide member, and/or the catheter(s) as described below. The camera can include any device suitable for capturing and transmitting an image via hard wire and/or wirelessly to a display. For example, if the camera is wired to a display, the wire connecting the camera to the display can have a distal end connected to the camera, a length disposed through the lumen 126 of the elongate tubular member 120 and the lumen 146 of the coil member 140, and a proximal end connected to a display device, memory device, and/or a receiver.

In use, the optical fiber 190 and/or camera enables a user to identify the placement of the guide member 100 within a bodily passage and allows the user to selectively navigate through the anatomy of a patient. For example, the user can identify placement of the guide member 100 by activating the light source 198 and locating the axially and/or radially-directed light emitting from the optical fiber 190. In another example, the user can navigate through the anatomy of a patient by rotating the fitting 180 and, therefore, the coil member 140 to advance the guide member 100 towards a point of treatment. When the coil member 140 includes curve 148, or multiple curves, the user can advantageously direct the distal end 144 of the coil member 140 selectively in the direction of the point of treatment. The inclusion of a rigid, or semi-rigid, elongate tubular member 120 in guide member 100 increases the torquability of the coil member 140, providing a user with the ability to navigate the anatomy of a patient.

FIGS. 2 and 2A illustrate an exemplary catheter 200 disposed over guide member 100. The catheter 200 comprises a proximal end 202, distal end 204, an elongate main body 220, a balloon 240, and a collar 250. While exemplary catheter 200 includes a balloon, any suitable medical device can be used in combination with the guide members described herein, and skilled artisans will be able to select a suitable medical device according to a particular embodiment based on various considerations, such as the desired procedure to be accomplished. Example medical devices considered suitable include, but are not limited to, catheters, irrigation catheters, balloon catheters, and any other suitable medical device.

The main body 220 comprises a proximal end 222, distal end 224 and a wall 225 that defines an inflation port 226, inflation lumen 228, guide member lumen 230, recess 232, and shoulder 234. The inflation lumen 228 extends between the inflation port 226 and an opening 227 disposed between the proximal end 222 and the distal end 224 of the main body 220. The guide member lumen 230 extends between the proximal end 222 and the distal end 224 of the main body 220.

The recess 232 extends from the proximal end 222 of the main body into the guide member lumen 230 towards the distal end 224 of the main body 220 and has a first diameter 235. The shoulder 234 extends radially into the recess 232 and defines a second diameter 237 that extends from the distal end of the recess 232 to the distal end 224 of the main body 220. The first diameter 235 of the recess 232 is greater than the second diameter 237 defined by the shoulder 234 and is configured to receive projection 160. The second diameter 237 is configured to receive a portion of the elongate tubular member 120 and the coil member 140 of the guide member 100.

Alternative to defining shoulder 234, the wall 225 of the main body 220 can define a tapered and/or sloped recess configuration adapted to limit the distal advancement of the projection 160 within the recess. Therefore, the configuration of the projection 160 and/or proximal end of the guide member lumen 230 can vary, and skilled artisans will be able to select an appropriate configuration for inclusion in a catheter according to a particular embodiment based on various considerations, such as the configuration of the projection, and/or guide member lumen, among others.

In a further alternative, the main body 220 can define a guide member lumen having a continuous inner diameter, such as when the fitting 180 is releasably attached to the proximal end 122 of the elongate tubular member 120 and the projection 160 has been omitted.

The guide member 100 is disposed within the guide member lumen 230 of the main body 220 such that projection 160 is disposed within the recess 232 of the guide member lumen 230 and fitting 180 is disposed proximal to the proximal end 222 of the main body 220. Projection 160 is adapted to interact with shoulder 234 to stop distal progression of the guide member 100 through the guide member lumen 230 when a distal force is placed on the guide member 100 (e.g., on fitting 180). In addition, projection 160 is adapted to interact with fitting 180 to stop proximal progression of the guide member 100 through the guide member lumen 230 when a proximal force is placed on the guide member 100 (e.g., on fitting 180). This structural arrangement advantageously allows the guide member 100 to be advanced distally and withdrawn proximally to assist in navigating the catheter 200 to a point of treatment. Furthermore, this structural arrangement advantageously provides a guide member 100 that is rotatable 360° within the guide member lumen 230 to assist a user in navigating the catheter 200 to a point of treatment. Alternatively, as described above, the projection 160 can be omitted and the fitting 180 can be releasably attached to the proximal end 124 of the elongate tubular member 120 so that any suitable medical device can be advanced over the guide member 100.

The distal end of the optical fiber 190 can be disposed at any suitable location along the length of the coil member 140 and/or elongate tubular member 120. For example, when disposed in the guide member lumen 230, the optical fiber 190 can be cut at a length which disposes its distal end 194 at a location distal to, proximal to, and/or at the distal end 224 of the main body 220.

Collar 250 is attached to the proximal end 222 of the main body 220 and defines a passageway 251 that permits movement of the elongate tubular member 120 therethrough and prevents, or substantially prevents, movement of the projection 160 therethrough. Thus, the collar 250 advantageously provides for retaining the projection 160 within the recess 232 of the main body 220 and stopping proximal progress of the guide member 100 when a proximal force is placed on the guide member 100 (e.g., fitting 180). In an alternative, collar 250 can be omitted, or provided separately.

Balloon 240 is attached to the distal end 224 of the main body 220 and is configured to move between a deflated configuration and an inflated configuration. The material of the balloon 240 and the portion of the exterior surface of the main body 220 positioned within the balloon 240 define an inflation chamber 242. The balloon 240 is positioned on the distal end 224 of the main body 220 such that opening 227 is in communication with the inflation chamber 242. With this structural arrangement, the balloon 240 can move between the deflated and inflated configurations as fluid is moved into and out of the inflation chamber 242 via the opening 227, inflation lumen 228, and inflation port 226.

A user inflates the balloon 240 by introducing a fluid (e.g., saline) into the inflation lumen 228 until the fluid passes through the opening 227 and into the inflation chamber 242. The resulting pressure placed on the inner surface of the balloon 240 by the fluid causes the balloon 240 to inflate and adopt the inflated configuration. To move the balloon 240 to the deflated configuration, vacuum pressure can be applied to the inflation lumen 228 to remove fluid located within the inflation chamber 242 via the opening 227, resulting in the balloon 240 collapsing and returning to a deflated configuration. FIG. 2 illustrate the balloon 240 in the inflated configuration.

It is considered advantageous to provide a coil member 140 and/or elongate tubular member 120 with a length sufficient to have to the distal end 144 of the coil member 140 extend distal to the distal end 224 of the main body 220 when the projection 160 is retracted proximally to interact with collar 250. Alternatively, a coil member 140 and/or elongate tubular member 120 with a length sufficient to have to the distal end 144 of the coil member 140 disposed proximal to the distal end 224 of the main body 220 when the projection 160 is retracted proximally to interact with collar 250 is considered suitable. Thus, the guide member 100 is moveable within the guide member lumen 230 between a first position and a second position. In the first position, the distal end 144 of the coil member 140 is disposed in the first coil position relative to the distal end 224 of the main body of the 220. In the second position, the distal end 144 of the coil member 140 is disposed in a second coil position relative to the distal end 224 of the main body 220. The first coil position being different from the second coil position.

The length of the guide member 100, elongate tubular member 120, coil member 140, and/or optical fiber 190 can vary depending on the configuration of the main body 220 and/or balloon 240. However, it is considered advantageous to have an elongate tubular member 120 with a length that positions the distal end 124 of the elongate tubular member 120 proximal to the proximal end of the balloon 240 to allow for flexibility through the balloon 240. For example, when projection 160 is advanced distally to interact with shoulder 234, the distal end 124 of the elongate tubular member 120 is disposed proximal to the proximal end of the balloon 240.

Alternative to main body 220 extending through the length of the balloon 240, as illustrated in FIG. 2, a balloon that defines a lumen that extends from an opening at the proximal end of the balloon to an opening at the distal end of the balloon can be attached to the distal end of the main body. In this embodiment, the distal end of the main body is located at, or near, the opening defined at the distal end of the inflation lumen. The balloon is attached to the distal end of the main body such that the lumen of the balloon is in communication with guide member lumen and advantageously allows for the coil member to be advanced through its length and navigate the balloon through tortuous passages. The material of the balloon, the wall of the lumen extending through the length of the balloon, and the portion of the exterior surface of the main body positioned within the balloon define an inflation chamber. The balloon is positioned on the distal end of the main body such that the opening at the distal end of the inflation lumen is in communication with the inflation chamber. With this structural arrangement, the balloon can move between the deflated and inflated configurations as fluid is moved into and out of the inflation chamber via the opening at the distal end of the inflation lumen, inflation lumen, and inflation port.

When a balloon defines a lumen that extends along its length, the guide member is disposed within the guide member lumen of the main body and the lumen of the balloon such that the projection is disposed within the recess of the guide member lumen and fitting is disposed proximal to the proximal end of the main body. This configuration advantageously allows the guide member to be advanced distally and withdrawn proximally to assist in navigating the catheter to a point of treatment. Furthermore, this configuration advantageously provides a guide member that is rotatable 360° within the guide member lumen and the lumen of the balloon to assist a user in navigating the catheter to a point of treatment. Alternatively, as described above, the projection can be omitted and the fitting can be releasably attached to the proximal end of the elongate tubular member so that any suitable medical device can be advanced over a length of the guide member.

Figure 3A:
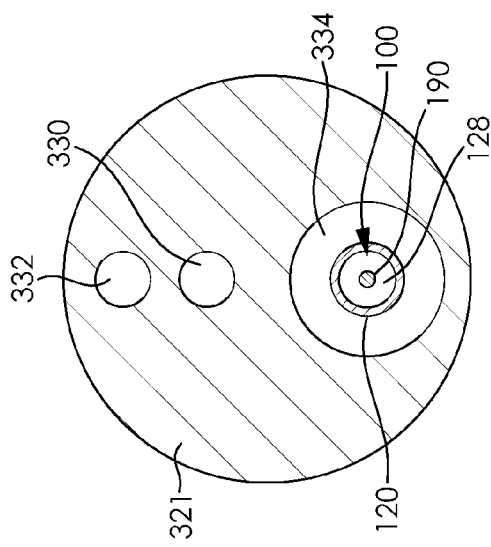
FIG. 3A is a sectional view of the catheter illustrated in FIG. 3, taken along line 3A-3A in FIG. 3.

FIGS. 3 and 3A illustrate another exemplary catheter 300 disposed over guide member 100. The catheter 300 is similar to the exemplary catheter 200 illustrated in FIG. 2, except as detailed below. The catheter 300 includes an elongate main body 320, a first balloon 340, and a second balloon 360.

The main body 320 comprises a proximal end 322, distal end 324, and a wall 321 that defines an inflation port 326, infusion port 328, inflation lumen 330, infusion lumen 332, guide member lumen 334, recess 336, shoulder 338, and collar 339. The inflation lumen 330 extends between the inflation port 326 and an opening 327 disposed between the proximal end 322 and the distal end 324 of the main body 320. The infusion lumen 332 extends between the infusion port 328 and a second opening 329 disposed between the proximal end 322 and the distal end 324 of the main body 320. The guide member lumen 334 extends between the proximal end 322 and the distal end 324 of the main body 320. The recess 336 extends from the proximal end 322 of the main body 320 into the guide member lumen 334 towards the distal end 324 of the main body 320 and has a first diameter 335. The shoulder 338 extends radially into the recess 336 and defines a second diameter 337 that extends from the distal end of the recess 336 to the distal end 324 of the main body 320. The first diameter 335 of the recess 336 is greater than the second diameter 337 defined by the shoulder 338 and is configured to receive projection 160. The second diameter 337 is sized to receive a portion of the elongate tubular member 120 and coil member 140 of the guide member 100.

The guide member 100 is disposed within the guide member lumen 334 of the main body 320 such that projection 160 is disposed within the recess 336 of the guide member lumen 334. Projection 160 is adapted to interact with shoulder 338 to stop distal progression of the guide member 100 through the guide member lumen 334 when a distal force is placed on the guide member 100 (e.g., on fitting 180), allowing the guide member 100 to be advanced and withdrawn to assist in advancing the catheter 300 to a point of treatment.

The first balloon 340 and second balloon 360 are disposed on the distal end 322 of the main body 320. The second balloon 360 is disposed within the first balloon 340. The material of the first balloon 340, the portion of the exterior surface of the main body 320 positioned within the first balloon 340, and the exterior surface of the second balloon 360 define an infusion chamber 342. The first balloon 340 is disposed on the distal end of the main body 320 such that the second opening 329 of the infusion lumen 332 is in communication with the infusion chamber 342. The material of the second balloon 360 and the portion of the exterior surface of the main body 320 positioned within the second balloon 360 define an inflation chamber 362. The second balloon 360 is disposed on the distal end 324 of the main body 320 such that the opening 327 of the inflation lumen 330 is in communication with the inflation chamber 362.

The second balloon 360 is adapted to move between deflated and inflated configurations as fluid is moved into and out of the inflation chamber 362 via the inflation port 326, inflation lumen 330 and the opening 327. A user inflates the second balloon 360 by introducing a fluid (e.g., saline) into the inflation port 326 and through the inflation lumen 328 until the fluid passes through the opening 327 into the inflation chamber 362. The resulting pressure placed on the inner surface of the second balloon 360 by the fluid causes the second balloon 360 to inflate and adopt the inflated configuration. To move the second balloon 360 to the deflated configuration, vacuum pressure can be applied to the inflation port 326 to remove fluid located within the inflation chamber 362, resulting in the second balloon 360 deflating.

Similar to the second balloon 360, the first balloon 340 is adapted to move between folded and expanded configurations by way of movement of the second balloon 360 between its inflated and deflated configurations. Thus, the user expands the first balloon 340 by inflating the second balloon 360. To move the first balloon 340 to the folded configuration, vacuum pressure can be applied to the inflation port 326 to remove fluid within the inflation chamber 362 resulting the second balloon 360 and the first balloon 340 returning to their deflated and folded configurations.

The first balloon 340 and second balloon 360 can advantageously include memory imparted onto the balloons by a heat treatment step that comprises heating the balloons while they are in their deflated and folded configurations. This heat treatment, and the resulting memory, gives the balloons a tendency to return to their deflated and folded configurations. Alternatively, the heat treatment step can be omitted or applied to one of the first balloon 340 or second balloon 360 independently. For example, when only the first balloon 340 has been heat treated, the first balloon 340 will have a tendency to return to its folded configuration when the second balloon 360 is moved from its inflated configuration to its deflated configuration.

The first balloon 340 includes one or more regions 344 that include one or more pores 346. Each of the pores 346 extends through the material of the first balloon 340 and permits fluid (e.g., medication) to pass through the wall of the first balloon 340, preferably with the application of pressure within the infusion chamber 342. Alternatively, when at least two or more pores 346 are provided, at least two of the pores 346 can vary in diameter. For example, the pores 346 can increase in diameter from the proximal end to the distal end of the first balloon 340. In a further alternative, when at least two or more pores 346 are provided, the pores 346 can increase in number from the proximal end to the distal end of the first balloon 340. The variable size and number configurations advantageously provide substantially equalized distribution and/or reduced pressure drop of the medication as it is being passed through the wall of the first balloon 340 from the proximal end to the distal end of the first balloon 340.

The regions 344 can be arranged on the first balloon 340 in any suitable configuration. For example, the regions 344 can circumferentially-extend around the first balloon 340. Other configurations considered suitable include a single circumferentially-extending region, multiple circumferentially-extending regions, a staggered configuration, and/or linear configuration along the length of the first balloon.

Depending on the size and number of pores 346 defined by the wall of the first balloon 340, the first balloon 340 can be adapted to move between folded and expanded configuration as medication is moved into and out of the infusion chamber 342 via the infusion port 328, infusion lumen 332 and the second opening 329. Configurations that allow for the first balloon 340 to move between a deflated and inflated configuration advantageously provide two different inflated configurations for the catheter 300. For example, a first configuration where the second balloon 360 is inflated and a second configuration wherein the first balloon 340 is inflated in combination with the second balloon 360.

While the catheter 300 has been described as including two balloons, a first outer balloon 340 and a second inner balloon 360, the catheter 300 can alternatively comprise a single balloon defining the one or more regions containing one or more pores as described above. When a single balloon is disposed on the distal end of the main body, the main body defines an infusion port and an infusion lumen and an opening disposed on the distal end of the inflation lumen. The single balloon is disposed on the distal end of the main body and the material of the balloon and the portion of the exterior surface of the main body disposed within the balloon define an infusion chamber. The balloon is positioned on the distal end of the main body such that the opening of the infusion lumen is in communication with the infusion chamber. The balloon is adapted to move between deflated and inflated configurations as medication is moved into and out of the infusion chamber via the infusion port, infusion lumen and opening. The amount of inflation of the balloon will depend on the number and diameter of the one or more pores defined by the wall of the balloon and the amount, and rate, of medication being introduced into the infusion chamber.

Additional structure can be attached to the catheters described herein to facilitate the inflation and deflation of the balloon(s). For example, a syringe or other suitable structure can be attached to the inflation port and/or infusion port using any suitable connection, such as a luer lock connection. The fluid and/or medication can be stored within the syringe, inflation lumen, and/or infusion lumen and can be introduced into and removed from the inflation chamber and/or infusion chamber by operating the syringe using conventional practices.

Alternative to main body 320 extending through the length of the balloon 340, as illustrated in FIG. 3, a balloon that defines a lumen that extends from an opening at the proximal end of the balloon to an opening at the distal end of the balloon can be attached to the distal end of the main body. In this embodiment, the distal end of the main body is located at, or near, the opening defined at the distal end of the inflation lumen. The balloon is attached to the distal end of the main body such that the lumen of the balloon is in communication with guide member lumen and advantageously allows for the coil member to be advanced through its length and navigate the balloon through tortuous passages. The material of the balloon, the wall of the lumen extending through the length of the balloon, and the portion of the exterior surface of the main body positioned within the balloon define an inflation chamber. The balloon is positioned on the distal end of the main body such that the opening at the distal end of the inflation lumen is in communication with the inflation chamber and the opening at the distal end of the infusion lumen is in communication with the infusion chamber. With this structural arrangement, the balloon can move between the deflated and inflated, and folded and expanded, configurations as fluid is moved into and out of the inflation chamber and infusion chamber via the opening at the distal end of the inflation lumen and the opening at the distal end of the infusion lumen.

When a balloon defines a lumen that extends along its length, the guide member is disposed within the guide member lumen of the main body and the lumen of the balloon such that the projection is disposed within the recess of the guide member lumen and fitting is disposed proximal to the proximal end of the main body. This configuration advantageously allows the guide member to be advanced distally and withdrawn proximally to assist in navigating the catheter to a point of treatment. Furthermore, this configuration advantageously provides a guide member that is rotatable 360° within the guide member lumen and the lumen of the balloon to assist a user in navigating the catheter to a point of treatment. Alternatively, as described above, the projection can be omitted and the fitting can be releasably attached to the proximal end of the elongate tubular member so that any suitable medical device can be advanced over a length of the guide member.

Figure 4:
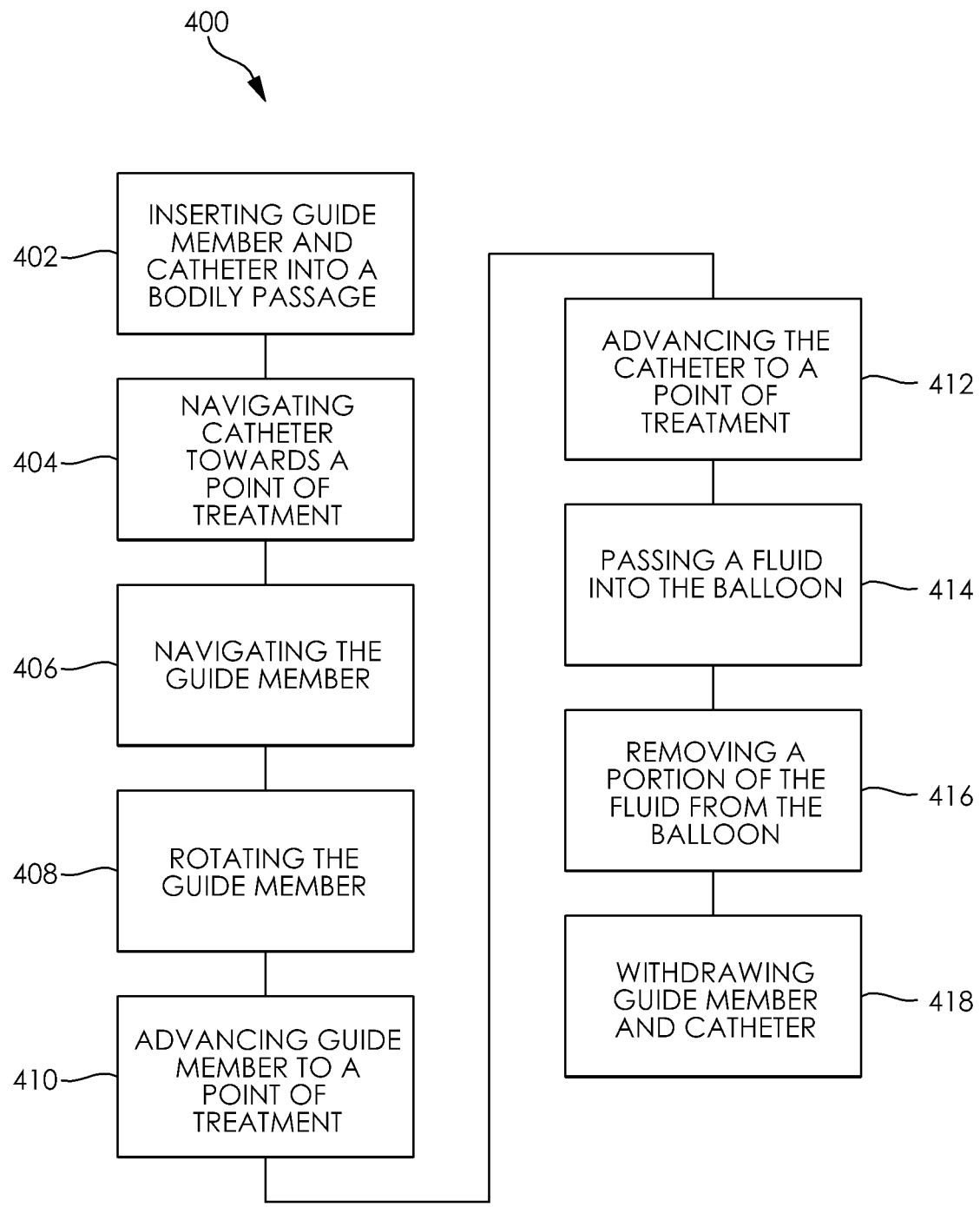
FIG. 4 is a flowchart representation of an exemplary method of treatment.

FIG. 4 is a flowchart representation of an exemplary method 400 of treating tissue in a bodily passage defined by a passage wall using the exemplary catheter and guide member described above with respect to FIG. 2. An initial step 402 comprises inserting a guide member and catheter each having a proximal end and a distal end into a bodily passage such that the distal end of the catheter is disposed in the bodily passage. Another step 404 comprises navigating the distal end of the catheter towards a point of treatment within said bodily passage. Another step 406 comprises navigating the distal end of the guide member towards a point of treatment. Another step 408 comprises rotating the guide member towards a point of treatment. Another step 410 comprises advancing the guide member to a point of treatment. Another step 412 comprises advancing the catheter to a point of treatment. Another step 414 comprises passing a fluid into the balloon. Another step 416 comprises removing a portion of the fluid from the balloon. Another step 418 comprises withdrawing the distal end of the guide member and catheter from the bodily passage.

The step of inserting the distal end of a catheter and guide member into a bodily passage can be accomplished using the exemplary catheter and guide member described above with reference to FIG. 2. However, while the exemplary catheter and guide member described above with reference to FIG. 2 has been described below as accomplishing the method of treatment associated with FIG. 4, other catheter configurations, and/or medical devices, such as those described herein can be utilized to accomplish the method of treatment associated with FIG. 4, and skilled artisans will be able to select an appropriate catheter and/or medical device according to a particular embodiment based on various considerations, such as the procedure intended to be accomplished, among others.

The step of navigating the distal end of the catheter towards a point of treatment can be accomplished transcutaneously, via display, and/or using direct visualization (e.g., with a scope). For example, when the distal end of the catheter comprises a light source and/or camera, navigating the distal end of the catheter towards a point of treatment can be accomplished transcutaneously and/or via live feed on a display. In an example, navigating the distal end of the catheter towards a point of treatment using transcutaneous visualization can be accomplished by visualizing the intensity of the light transcutaneously to determine if the intensity is indicative of proper positioning of the distal end of the catheter being directed towards a point of treatment. In another example, navigating the distal end of the catheter towards a point of treatment can be accomplished by viewing images provided on a display and determining if the images indicate proper positioning of the distal end of the catheter being direct towards a point of treatment.

The step of navigating the distal end of the guide member towards a point of treatment can be accomplished by applying a proximal or distal force on the guide member (e.g., fitting 180) to advance the guide member in the proximal or distal direction. For example, if it is determined in the step of navigating the distal end of the catheter towards a point of treatment that the distal end of the catheter is not properly positioned, the user can navigate the guide member in the proximal or distal direction to position the distal end of the guide member at a location suitable to advance the catheter towards a point of treatment. In another example, the user may determine that anatomical features are blocking the advancement of the distal end of the catheter (e.g., vocal chords) and/or that the distal end of the catheter must be navigated through an opening positioned at an angle from which the distal end of the catheter is currently disposed. In this example, the user can navigate the guide member in a proximal or distal direction to position the guide member in a location suitable to advance the catheter towards a point of treatment around the anatomical features or through the opening.

The step of rotating the guide member towards a point of treatment can be accomplished by rotating the guide member (e.g., fitting 180) in a clockwise or counterclockwise direction around the lengthwise axis of the elongate tubular member. For example, if it is determined in the step of navigating the distal end of the catheter towards a point of treatment and/or the step of navigating the guide member towards a point of treatment that the distal end of the catheter is not properly positioned at a point of treatment and the point of treatment is beyond a passageway located in the wall of the bodily passage, the user can rotate the fitting in either the clockwise or counterclockwise direction around the lengthwise axis of the elongate tubular member to position the distal end of the guide member towards the point of treatment through the passageway.

Depending on the location of the distal end of the catheter within the bodily passage and its position with respect to the intended point of treatment, the steps of navigating the guide member towards a point of treatment and/or rotating the guide member towards a point of treatment can be omitted, combined, or one of the steps can be omitted.

The step of advancing the guide member to a point of treatment can be accomplished by advancing the guide member distally and can be confirmed transcutaneously, via video display, or using direct visualization (e.g., with a scope).

The step of advancing the catheter to a point of treatment can be accomplished by advancing the catheter over the previously navigated guide member and can be confirmed transcutaneously, via video display, or using direct visualization (e.g., with a scope). Alternative to advancing the catheter to a point of treatment, the guide member can be advanced distally to cannulate the bodily passage with the coil member. In a further alternative, the guide member can be advanced distally to cannulate the bodily passage and then the step of advancing the catheter to a point of treatment can be accomplished. Optionally, the steps of advancing the guide member to a point of treatment and advancing the catheter to a point of treatment can be accomplished concurrently.

The step of passing a fluid through the inflation lumen is accomplished by passing a fluid (e.g., saline, water, contrast, mixture of one or more of saline, water, and/or contrast) through the inflation lumen and into the inflation chamber of the balloon with a pressure sufficient to inflate the balloon and provide contact between a portion, the entirety, or the majority, of the exterior surface of the balloon and the passage wall. The amount of saline introduced into the inflation chamber will determine the amount of inflation of the balloon. For example, in procedures where a large amount of contact and pressure are desired between the exterior surface of the balloon and the passage wall, a larger amount of fluid will be passed through the inflation port into the inflation chamber. In another example, in procedures where a smaller amount of contact and pressure are desired between the exterior surface of the balloon and the passage wall, a smaller amount of fluid will be passed through the inflation port into the inflation lumen. Examples of pressures considered suitable include pressures in the range from about 1 ATM to about 12 ATM. A pressure gauge, or other similar device, can be used to provide a user with the ability to view the amount of pressure being applied at a point of treatment.

The step of removing a portion of the fluid from the balloon can be accomplished by removing a portion, the entity, or majority, of the fluid passed into the inflation chamber. For example, a syringe in communication with the inflation port can be used to provide vacuum pressure to remove the fluid from the inflation chamber.

The step of withdrawing the distal end of the guide member and catheter from the bodily passage can be accomplished by pulling the catheter and guide member proximally until they are completely removed from the bodily passage and the patient.

Optional steps of inserting the distal end of a cutting tool into the bodily passage, navigating the distal end of the cutting tool to a point of treatment, cutting tissue from the bodily passage, removing the tissue, and withdrawing the cutting tool can be accomplished prior to inserting the distal end of a catheter into a bodily passage. Any suitable cutting tool can be used to accomplish these steps. For example, the cutting tool can comprise a suction cutter or scalpel. To accomplish these steps, an initial step comprises inserting the distal end of a cutting tool into a bodily passage. Another step comprises navigating the distal end of the cutting tool to a point of treatment. The step of navigating the distal end of a cutting tool to a point of treatment can be accomplished using direct and/or transcutaneous visualization. Another step comprises cutting tissue from the bodily passage. Another step comprises removing the tissue from the bodily passage. Another step comprises removing the distal end of the cutting tool from the bodily passage.

While various catheter configurations, steps, alternative steps, and optional steps have been described above with respect to treating tissue in a bodily passage, these catheter configurations, steps, alternative steps, and optional steps can be included in, accomplished concurrently with, and/or accomplished in the alternative to, the methodologies, catheter configurations, steps, alternative steps, and/or optional steps described below with respect to treating tissue in a bodily passage, sinus cavity, airway, and/or sinus passage.

Figure 5:
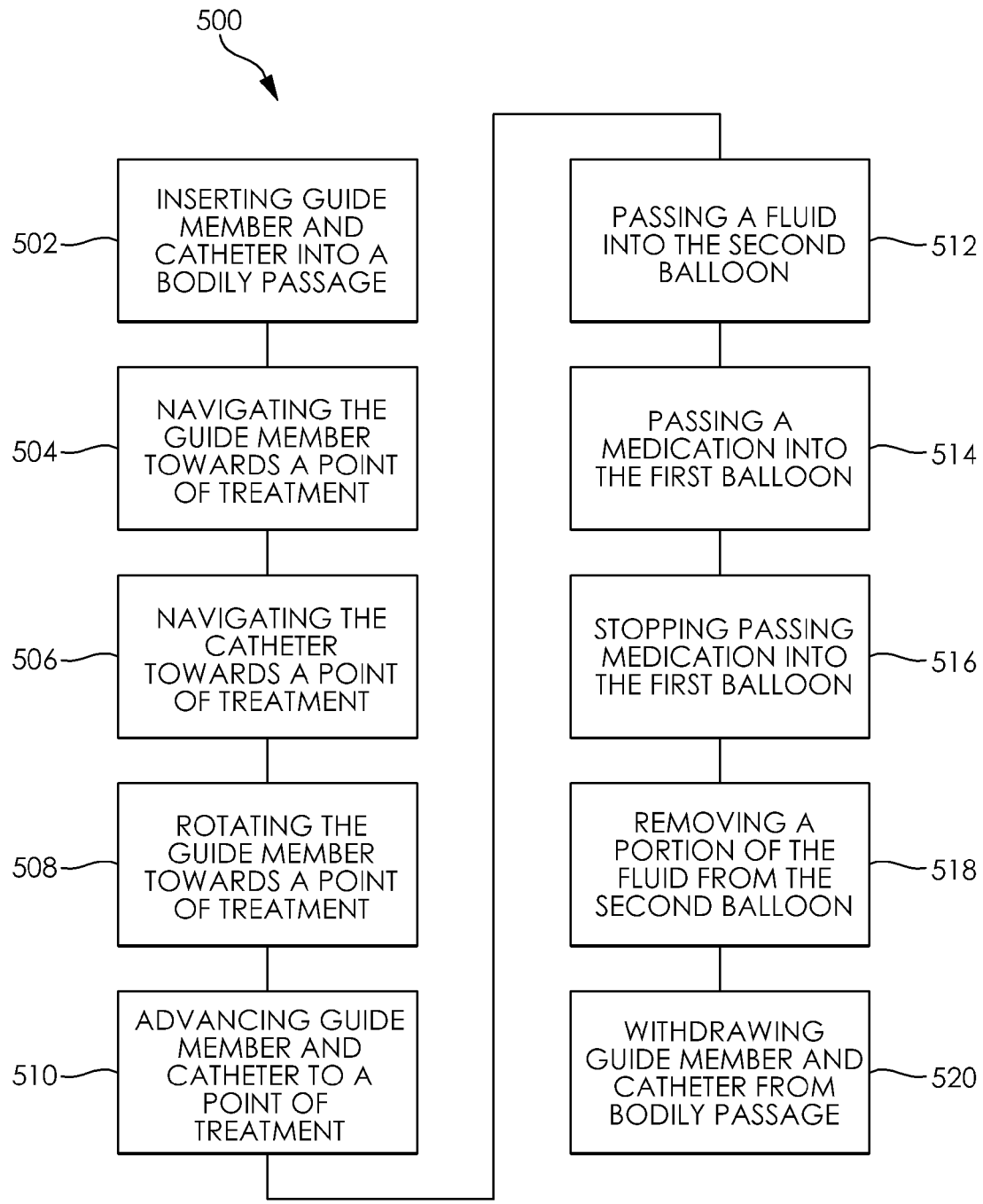
FIG. 5 is a flowchart representation of another exemplary method of treatment.

FIG. 5 is a flowchart representation of another exemplary method 500 of treating tissue in a bodily passage defined by a passage wall using the exemplary catheter and guide member described above with respect to FIG. 3. The method 500 is similar to that described above with respect to method 400, except as described below. An initial step 502 comprises inserting a guide member and catheter each having a proximal end and a distal end into a bodily passage such that the distal end of the catheter is disposed in the bodily passage. Another step 504 comprises navigating the distal end of the guide member towards a point of treatment. Another step 506 comprises navigating the distal end of the catheter towards a point of treatment within said bodily passage. Another step 508 comprises rotating the guide member towards a point of treatment. Another step 510 comprises advancing the guide member and catheter to a point of treatment. Another step 512 comprises passing a fluid through the inflation lumen and into the second balloon with a pressure sufficient to inflate the second balloon and provide contact between a portion of the first balloon and the passage wall. Another step 514 comprises passing a medication through the infusion lumen and into the first balloon with a pressure sufficient to expel the medication through one or more pores. Another step 516 comprises stopping the passing a medication through the infusion lumen and into the first balloon. Another step 518 comprises removing a portion of the fluid from the second balloon. Another step 520 comprises withdrawing the distal end of the guide member and catheter from the bodily passage.

The step of inserting the distal end of a guide member and catheter into a bodily passage can be accomplished using the exemplary guide member and catheter described above with reference to FIG. 3. However, while the exemplary guide member and catheter described above with reference to FIG. 3 has been described below as accomplishing the method of treatment associated with FIG. 5, other catheter configurations, and/or medical devices, such as those described herein can be utilized to accomplish the method of treatment associated with FIG. 5, and skilled artisans will be able to select an appropriate catheter and/or medical device according to a particular embodiment based on various considerations, such as the procedure intended to be accomplished, among others.

The step of advancing the guide member and catheter to a point of treatment can be accomplished as a single step or can be completed as two separate steps. For example, alternative to accomplishing the step of advancing the catheter and guide member to a point of treatment, a step comprising advancing the guide member to a point of treatment and a step of advancing the catheter to a point of treatment can be accomplished separately.

The step of passing a fluid through the inflation lumen and into the second balloon with a pressure sufficient to inflate the second balloon and provide contact between a portion of, the entirety of, or a majority of, the first balloon and the passage wall can be accomplished by introducing a fluid into the inflation port to advance the second balloon from its deflated to its inflated configuration. The amount of the exterior surface of the first balloon contacting the passage wall, and the amount of pressure exerted by the exterior surface of the first balloon onto the passage wall, will depend on the amount fluid being passed into the inflation chamber of the second balloon. For example, in procedures where a large amount of contact and pressure are desired between the exterior surface of the first balloon and the passage wall, a larger amount of fluid will be passed through the inflation port into the inflation chamber. In another example, in procedures where a smaller amount of contact and pressure are desired between the exterior surface of the first balloon and the passage wall, a smaller amount of fluid will be passed through the inflation port into the inflation chamber. Examples of pressures considered suitable include pressures in the range from about 1 ATM to about 12 ATM.

The step of passing a medication through the infusion lumen into the first balloon with a pressure sufficient to expel the medication through the one or more pores can be accomplished by passing a medication through the infusion port and infusion lumen. This step can be accomplished prior, during, or subsequent to passing a fluid into the inflation chamber. The medication can be passed into the infusion lumen using any suitable device (e.g., a syringe in communication with the infusion lumen). By inflating the second balloon to a pressure suitable to provide contact between the exterior surface of the first balloon and the passage wall, the medication being expelled by the one or more pores can advantageously be infused into the passage wall defining the bodily passage. It is considered advantageous to pass medication through the infusion lumen and into the first balloon while the second balloon is in its inflated configuration to infuse the medication within the passage wall.

For example, in procedures where it is desired to infuse a larger amount of medication at a point of treatment, a larger amount of fluid will be passed through the inflation port into the inflation chamber. Thus, providing a larger amount of contact and pressure between the exterior surface of the first balloon and the passage wall. In another example, in procedures where it is desired to infuse a smaller amount of medication at a point of treatment, a smaller amount of fluid will be passed through the inflation portion into the inflation chamber. Thus, providing a smaller amount of contact and pressure between the exterior surface of the first balloon and the passage wall. Examples of pressures considered suitable to expel the medication through the one or more pores and infuse the medication into the wall defining the bodily passage include pressures in the range from about 1 ATM to about 10 ATM. Skilled artisans will appreciate however, that the pressure required to infuse the medication will correlate with the inflated pressure of the first balloon.

The medication can comprise any suitable fluid, drug, and/or agent used to treat a patient. Examples of medications considered suitable include, but are not limited to, anti-inflammatories (e.g., steroids), antineoplastics (e.g., mitomycin), cytotoxics, adrenaline (e.g., epinephrine), antibiotics, antifungal agents, and/or anti-proliferatives (e.g., such as those used on coronary stents), or a combination thereof.

While the steps of advancing the distal end of the catheter to a point of treatment within said bodily passage, passing a fluid through the inflation lumen and into the second balloon with a pressure sufficient to inflate the second balloon, and provide contact between a portion of the first balloon and the passage wall, and passing a medication through the infusion lumen into the first balloon with a pressure sufficient to expel the medication through one or more pores have been described as separate steps, these steps can be accomplished concurrently. In an alternative, the step of passing a medication through the infusion lumen into the first balloon with a pressure sufficient to expel the medication through one or more pores can be accomplished prior to or concurrently with the step of passing a fluid through the inflation lumen and into the second balloon with a pressure sufficient to inflate the second balloon and provide contact between a portion of the first balloon and the passage wall and/or the step of navigating the distal end of the catheter to a point of treatment within said bodily passage.

The step of stopping the step of passing a medication through the infusion lumen and into the first balloon can be accomplished by terminating the passing of the medication through the infusion lumen. In an example where a syringe is the device passing the medication into the infusion lumen, this can be accomplished by the user removing pressure from the plunger of the syringe.

While the steps of stopping the step of passing a medication through the infusion lumen and into the first balloon and removing a portion of the fluid from the second balloon have been described as separate steps, these steps can be accomplished concurrently. In another alternative, the step of stopping the step of passing a medication through the infusion lumen and into the first balloon can be accomplished prior to the step of removing a portion of the fluid from the second balloon.

While the steps of passing a medication through the infusion lumen into the first balloon with a pressure sufficient to expel the medication through one or more pores, removing a portion of the fluid from the second balloon, and withdrawing the distal end of the catheter from the bodily passage have been described as separate steps, these steps can be accomplished concurrently. In another alternative, the steps of passing a medication through the infusion lumen into the first balloon with a pressure sufficient to expel the medication through one or more pores and removing a portion of the fluid from the second balloon can be accomplished concurrently and the step of withdrawing the distal end of the catheter can subsequently be accomplished. In another alternative, the step of passing a medication through the infusion lumen into the first balloon with a pressure sufficient to expel the medication through one or more pores can be accomplished and the steps of removing a portion of the fluid from the second balloon and withdrawing the distal end of the catheter from the bodily passage can be accomplished subsequently and concurrently.

Optionally, the step of stopping the step of passing a medication through the infusion lumen and into the first balloon can be accomplished and the steps removing a portion of the fluid from the second balloon and withdrawing the distal end of the catheter from the bodily passage can be accomplished concurrently.

An optional step comprising inflating the second balloon to a pressure sufficient to damage the passage wall surrounding the exterior surface of the first balloon can also be included in the method of treatment. This step can be performed after, or replace, the step of passing a fluid through the inflation lumen and into the second balloon with a pressure sufficient to inflate the second balloon and provide contact between a portion of the first balloon and the passage wall. This step can be accomplished by inflating the second balloon to a pressure in the range from about 2 ATM to about 18 ATM. It is considered advantageous to damage the passage wall to create a larger anatomical passageway. An additional optional step comprises reducing the pressure of the second balloon after damaging the passage wall to a pressure sufficient to provide contact between a portion of the first balloon and the passage wall. This step can be accomplished by removing a portion of the fluid from the inflation chamber until a desired pressure is reached.

While various catheter configurations, steps, alternative steps, and optional steps have been described above with respect to treating tissue in a bodily passage, these catheter configurations, steps, alternative steps, and optional steps can be included in, accomplished concurrently with, and/or accomplished in the alternative to, the methodologies, catheter configurations, steps, alternative steps, and/or optional steps described above and/or below with respect to treating tissue in a sinus cavity, airway, and/or sinus passage.

Figure 6:
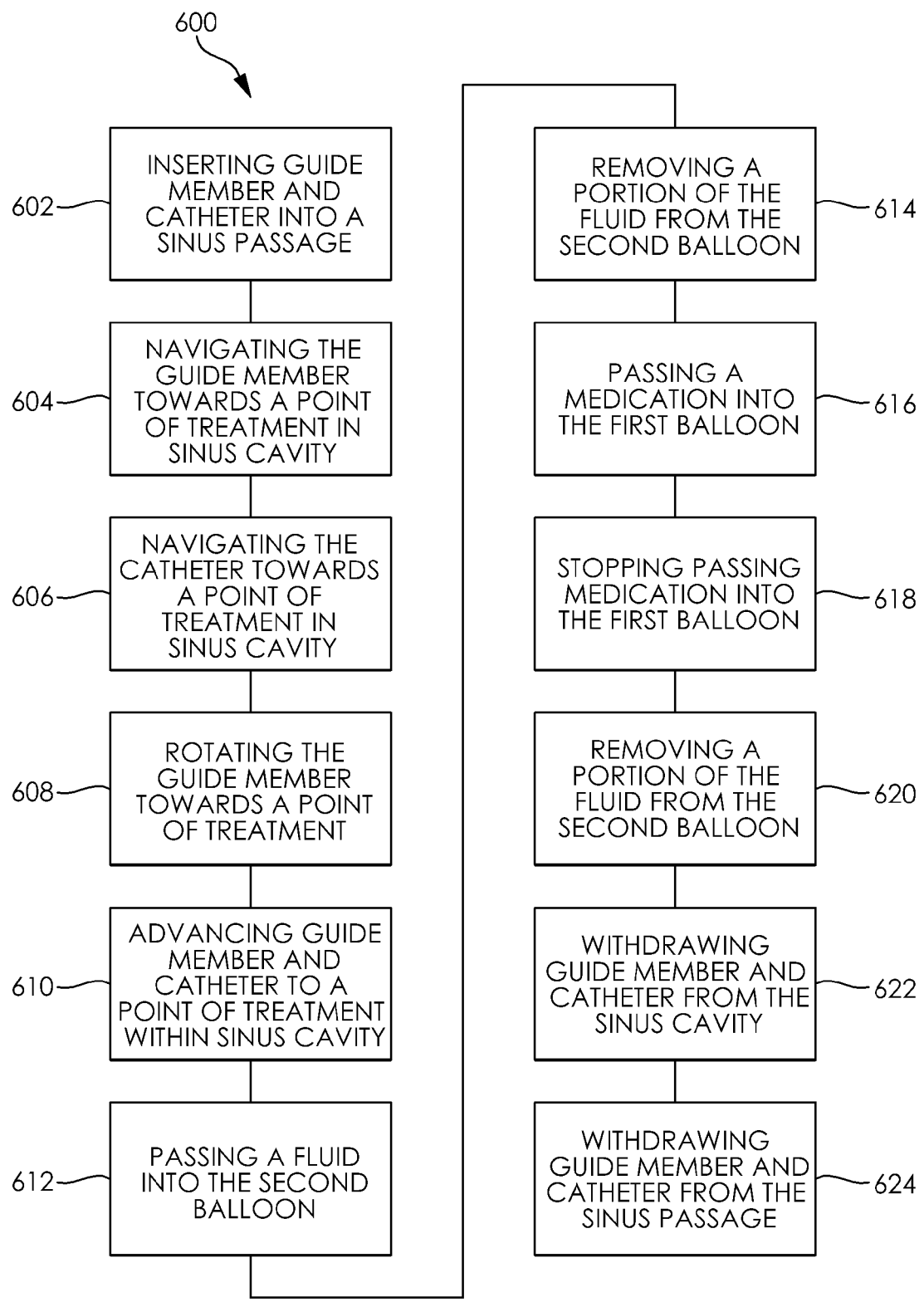
FIG. 6 is a flowchart representation of another exemplary method of treatment.

FIG. 6 is a flowchart representation of an exemplary method 600 of treating tissue in a sinus cavity defined by a cavity wall. The method 600 is similar to that described above with respect to method 500, except as described below. An initial step 602 comprises inserting a guide member and catheter each having a proximal end and a distal end into a sinus passage such that the distal end of a catheter is disposed in the sinus passage of a patient. Another step 604 comprises navigating the distal end of the guide member towards a point of treatment in a sinus cavity. Another step 606 comprises navigating the distal end of the catheter towards a point of treatment within a sinus cavity. Another step 608 comprises rotating the guide member towards a point of treatment. Another step 610 comprises advancing the guide member and catheter to a point of treatment. Another step 612 comprises passing a fluid through the inflation lumen and into the second balloon with a pressure sufficient to inflate the second balloon and damage the cavity wall. Another step 614 comprises removing a portion of the fluid from the second balloon to a pressure sufficient to provide contact between a portion of the first balloon and the cavity wall to allow medication to be delivered through the pores of the first balloon. Another step 616 comprises passing a medication through the infusion lumen and into the first balloon with a pressure sufficient to expel the medication through the one or more pores. Another step 618 comprises stopping the step of passing a medication through the infusion lumen and into the first balloon. Another step 620 comprises removing a portion of the fluid from the second balloon. Another step 622 comprises withdrawing the distal end of the guide member and catheter from the sinus cavity. Another step 624 comprises withdrawing the distal end of the guide member and catheter from the sinus passage.

The sinus passage and/or cavity wall can be treated using any of the herein described methods and/or steps by advancing the distal end of one or more of the devices described herein through a primary ostium, an accessory ostium, and/or a ventilation tube disposed in a cavity wall. For example, the step of advancing the catheter to a point of treatment can be accomplished by advancing the catheter over the previously cannulated guide member 100 to a point of treatment.

The step of rotating the guide member towards a point of treatment can be accomplished, as described above, and includes rotating the distal end of the coil member towards the face of a patient to confirm placement of the distal end of the catheter in the proper sinus cavity. For example, when treating the frontal sinus, the guide member can be rotated towards the forehead of the patient to allow the user to confirm proper placement of the guide member in the frontal sinus.

The steps of passing a fluid through the inflation lumen and into the second balloon with a pressure sufficient to inflate the second balloon and damage the cavity wall and removing fluid from the second balloon to a pressure sufficient to provide contact between a portion of the first balloon and the cavity wall are both optional. For example, in an alternative method, the steps of passing a fluid through the inflation lumen and into the second balloon with a pressure sufficient to inflate the second balloon and damage the cavity wall and removing fluid from the second balloon to a pressure sufficient to provide contact between a portion of the first balloon and the cavity wall can be omitted and replaced with a step comprising passing a fluid through the inflation lumen and into the second balloon with a pressure sufficient to inflate the second balloon and provide contact between a portion of the first balloon and the cavity wall. It is considered advantageous to pass medication through the infusion lumen into the first balloon when the second balloon is in its inflated configuration (e.g., damaging the cavity wall and/or contacting the cavity wall) so that the medication can be infused within the cavity wall. The step of passing fluid through the inflation lumen and into the second balloon with a pressure sufficient to inflate the second balloon and provide contact between a portion of the first balloon and the cavity wall can be accomplished by inflating the second balloon to a pressure in the range from about 1 ATM to about 12 ATM.

In a further alternative, the step of passing a fluid through the inflation lumen and into the second balloon with a pressure sufficient to inflate the second balloon and damage the cavity wall can be accomplished and the step of removing fluid from the second balloon to a pressure sufficient to provide contact between a portion of the first balloon and the cavity wall can be omitted. This advantageously allows for the infusion of medication while the second balloon is inflated to a pressure sufficient to damage the cavity wall.

While various catheter configurations, steps, alternative steps, and optional steps have been described above with respect to treating tissue in a sinus cavity, these catheter configurations, steps, alternative steps, and optional steps can be included in, accomplished concurrently with, and/or accomplished in the alternative to, the methodologies, catheter configurations, steps, alternative steps, and/or optional steps described above and/or below with respect to treating tissue in a bodily passage, airway, and/or sinus passage.

Figure 7:
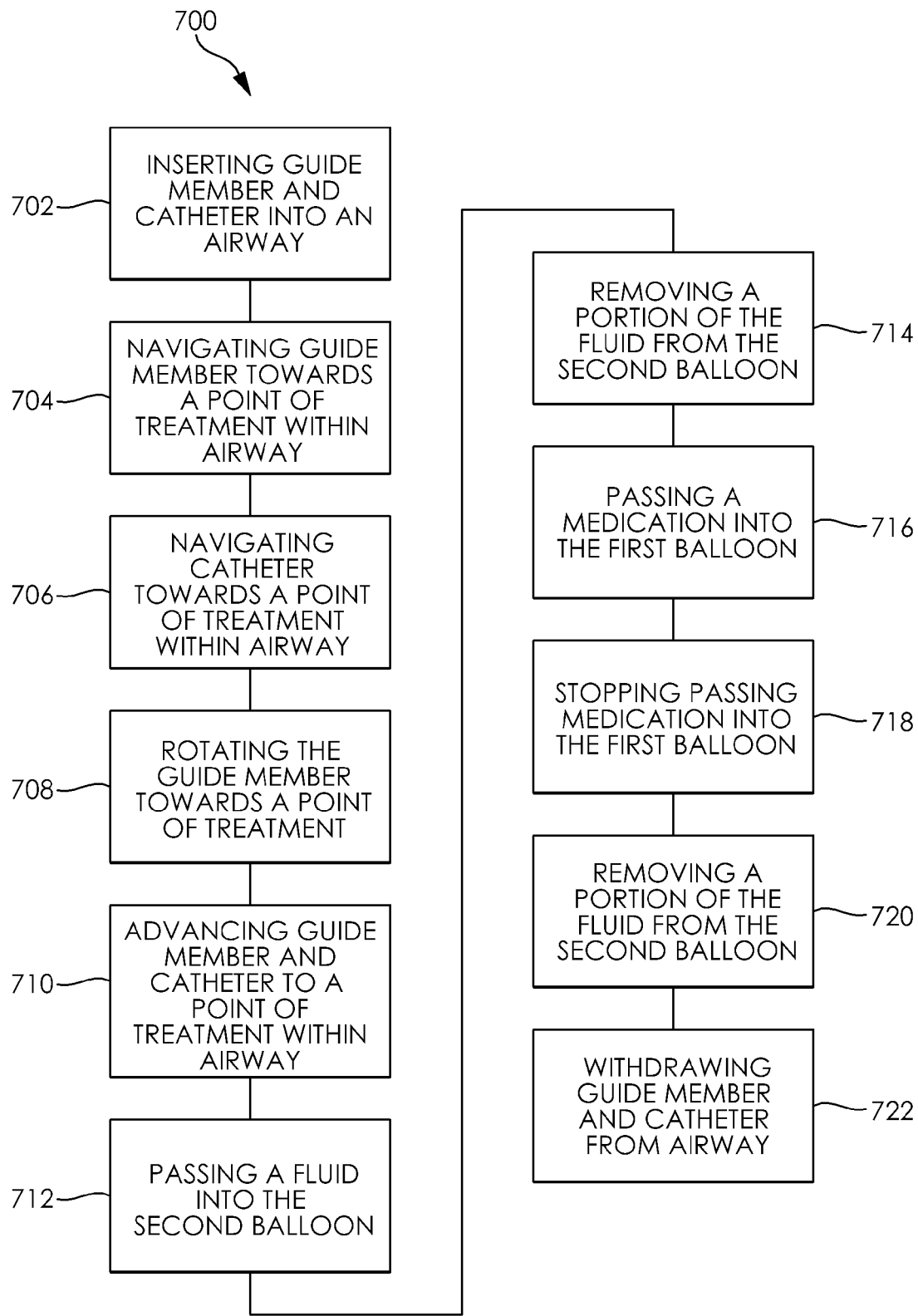
FIG. 7 is a flowchart representation of another exemplary method of treatment.

FIG. 7 is a flowchart representation of an exemplary method 700 of treating tissue within an airway defined by an airway wall. The method 700 is similar to that described above with respect to method 500, except as described below. An initial step 702 comprises inserting a guide member and catheter each having a proximal end and a distal end into an airway such that the distal end is disposed in the airway. Another step 704 comprises navigating the distal end of the guide member towards a point of treatment with the airway. Another step 706 comprises navigating the distal end of the catheter towards a point of treatment within the airway. Another step 708 comprises rotating the guide member towards a point of treatment. Another step 710 comprises advancing the guide member and catheter to a point of treatment within the airway. Another step 712 comprises passing a fluid through the inflation lumen and into the second balloon with a pressure sufficient to inflate the second balloon and dilate the point of treatment within the airway. Another step 714 comprises removing a portion of the fluid within the second balloon to a pressure sufficient to provide contact between a portion of the first balloon and the airway wall. Another step 716 comprises passing a medication through the infusion lumen and into the first balloon with a pressure sufficient to expel the medication through the one or more pores. Another step 718 comprises stopping passing the medication through the infusion lumen. Another step 720 comprises removing a portion of the fluid from the second balloon. Another step 722 comprises withdrawing the distal end of the guide member and catheter from the airway.

The step of dilating the second balloon to a pressure sufficient to dilate the point of treatment (e.g., stricture) can be accomplished by inflating the second balloon to a pressure in the range from about 2 ATM to about 12 ATM.

The steps of passing a fluid through the inflation lumen and into the second balloon with a pressure sufficient to inflate the second balloon and dilate the point of treatment within the airway and removing a portion of the fluid within the second balloon to a pressure sufficient to provide contact between a portion of the first balloon and the airway wall are both optional. For example, in an alternative, the steps of passing a fluid through the inflation lumen and into the second balloon with a pressure sufficient to inflate the second balloon and dilate the point of treatment within the airway and removing a portion of the fluid within the second balloon to a pressure sufficient to provide contact between a portion of the first balloon and the airway wall can be omitted and replaced with a step comprising passing a fluid through the inflation lumen and into the second balloon with a pressure sufficient to provide contact between a portion of the first balloon and the airway wall. It is considered advantageous to pass medication through the infusion lumen into the first balloon when the second balloon is in its inflated configuration (e.g., dilating the airway wall and/or contacting the airway wall) so that the medication can be infused within the airway wall.

In a further alternative, the step of passing a fluid through the inflation lumen and into the second balloon with a pressure sufficient to inflate the second balloon and dilate the point of treatment within the airway can be accomplished and the step of removing a portion of the fluid within the second balloon to a pressure sufficient to provide contact between a portion of the first balloon and the airway wall can be omitted. This advantageously allows for the infusion of medication while the second balloon is inflated to a pressure sufficient to dilate the point of treatment (e.g., a stricture).

The methods described herein can alternatively be used to treat one or more strictures within an airway. For example, the step of advancing the distal end of the catheter to a point of treatment within said airway comprises navigating the distal end past the stricture within the airway. Furthermore, the step of passing a fluid through the inflation lumen and into the second balloon with a pressure sufficient to inflate the second balloon and dilate the point of treatment within the airway can comprise dilating a stricture within an airway. While the step of advancing the distal end of the catheter past a stricture has been described, the distal end of the catheter can alternatively be navigated proximal to, or within, the stricture.

While various catheter configurations, steps, alternative steps, and optional steps have been described above with respect to treating tissue in an airway, these catheter configurations, steps, alternative steps, and optional steps can be included in, accomplished concurrently with, and/or accomplished in the alternative to, the methodologies, catheter configurations, steps, alternative steps, and/or optional steps described above/or below with respect to treating tissue in a bodily passage, sinus cavity, airway, and/or sinus passage.

Figure 8:
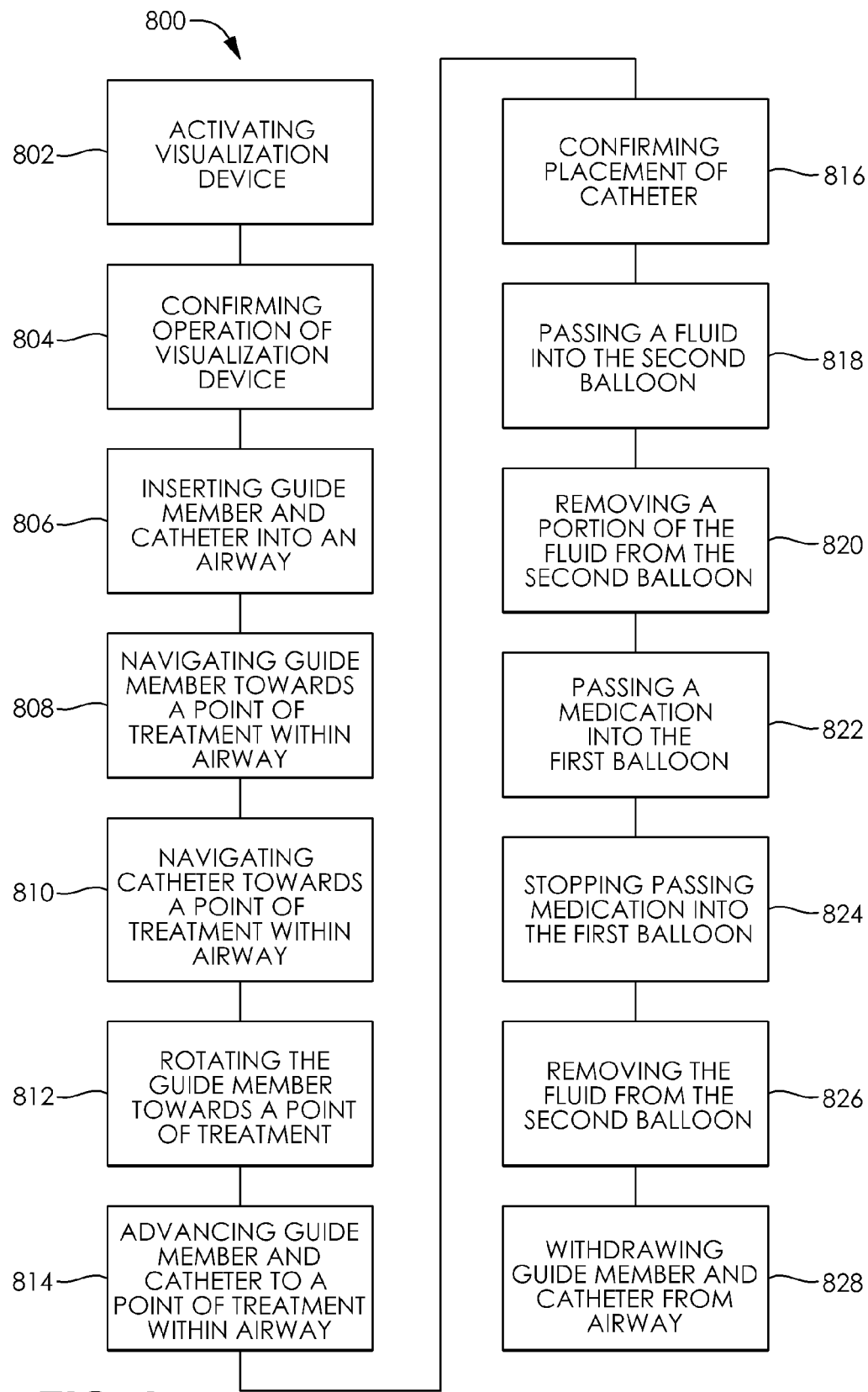
FIG. 8 is a flowchart representation of another exemplary method of treatment.

FIG. 8 is a flowchart representation of an exemplary method 800 of treating tissue within an airway defined by an airway wall. The method 800 is similar to that described above with respect to method 700, except as described below. An initial step 802 comprises activating a visualization device. Another step 804 comprises confirming operation of the visualization device. Another step 806 comprises inserting a guide member and catheter each having a proximal end and a distal end into an airway such that the distal end of the catheter is disposed in the airway. Another step 808 comprises navigating the distal end of the guide member towards a point of treatment within the airway. Another step 810 comprises navigating the distal end of the catheter towards a point of treatment within the airway. Another step 812 comprises rotating the guide member towards a point of treatment. Another step 814 comprises advancing the guide member and catheter to a point of treatment. Another step 816 comprises confirming placement of the catheter. Another step 818 comprises passing a fluid through the inflation lumen and into the second balloon with a pressure sufficient to inflate the second balloon and dilate the point of treatment within the airway. Another step 820 comprises removing a portion of the fluid within the second balloon to a pressure sufficient to provide contact between a portion of the first balloon and the airway wall. Another step 822 comprises passing a medication through the infusion lumen and into the first balloon with a pressure sufficient to expel the medication through the one or more pores. Another step 824 comprises stopping passing the medication through the infusion lumen. Another step 826 comprises removing the fluid from the second balloon. Another step 828 comprises withdrawing the distal end of the guide member and catheter from the airway.

The step of activating a visualization device can be accomplished by activating a light source associated with an optical fiber disposed within the catheter and/or activating a camera disposed within the catheter. The optical fiber and/or camera can be disposed on an interior surface of a lumen of the catheter, embedded within the wall of the catheter, and/or disposed on an exterior surface of the catheter. When an optical fiber is disposed within the catheter, the light source is adapted to be attached to the optical fiber, which is adapted to emit light radially and/or axially from the distal end of the optical fiber. When a camera is disposed within the catheter, the camera is adapted to capture images from the distal end of the catheter and/or from the circumference of the catheter at any point along the catheter length. The camera is adapted to be attached to a display and/or power source and can provide still and/or live footage to the display for review by the user. Alternatively, multiple cameras can be used in conjunction with, or separate from, one another. The camera can comprise a wired or wireless camera that can transmit images to a display and/or a storage device.

The step of confirming operation of the visualization device can be accomplished by the user verifying that light is being emitted from the optical fiber when the light source has been activated and/or the user verifying that the camera is capturing images and displaying the images on a display when the camera has been activated. The light source and/or camera can be disposed in the lumen defined by the guide member and/or a lumen defined by the catheter, or other medical device, such as those described herein.

The step of confirming placement of the catheter can be accomplished transcutaneously and/or via images provided on a display. In an example, confirming proper placement of the distal end of the catheter at a point of treatment using transcutaneous visualization can be accomplished by visualizing the intensity of the light being emitted from the optical fiber transcutaneously to determine if the intensity is indicative of proper positioning of the distal end of the catheter. In another example, confirming proper placement of the distal end of the catheter at a point of treatment can be accomplished by viewing images provided on a display and determining if the images indicate proper positioning of the distal end of the catheter at a point of treatment. If the distal end is confirmed as being properly placed at a point of treatment, the step ends. However, if it is determined that placement of the distal end of the catheter is not proper, further navigation of the distal end of the catheter may be necessary.

While various catheter configurations, steps, alternative steps, and optional steps have been described above with respect to treating tissue in an airway, these catheter configurations, steps, alternative steps, and optional steps can be included in, accomplished concurrently with, and/or accomplished in the alternative to, the methodologies, catheter configurations, steps, alternative steps, and/or optional steps described above and/or below with respect to treating tissue in a bodily passage, sinus cavity, airway, and/or sinus passage.

Figure 9:
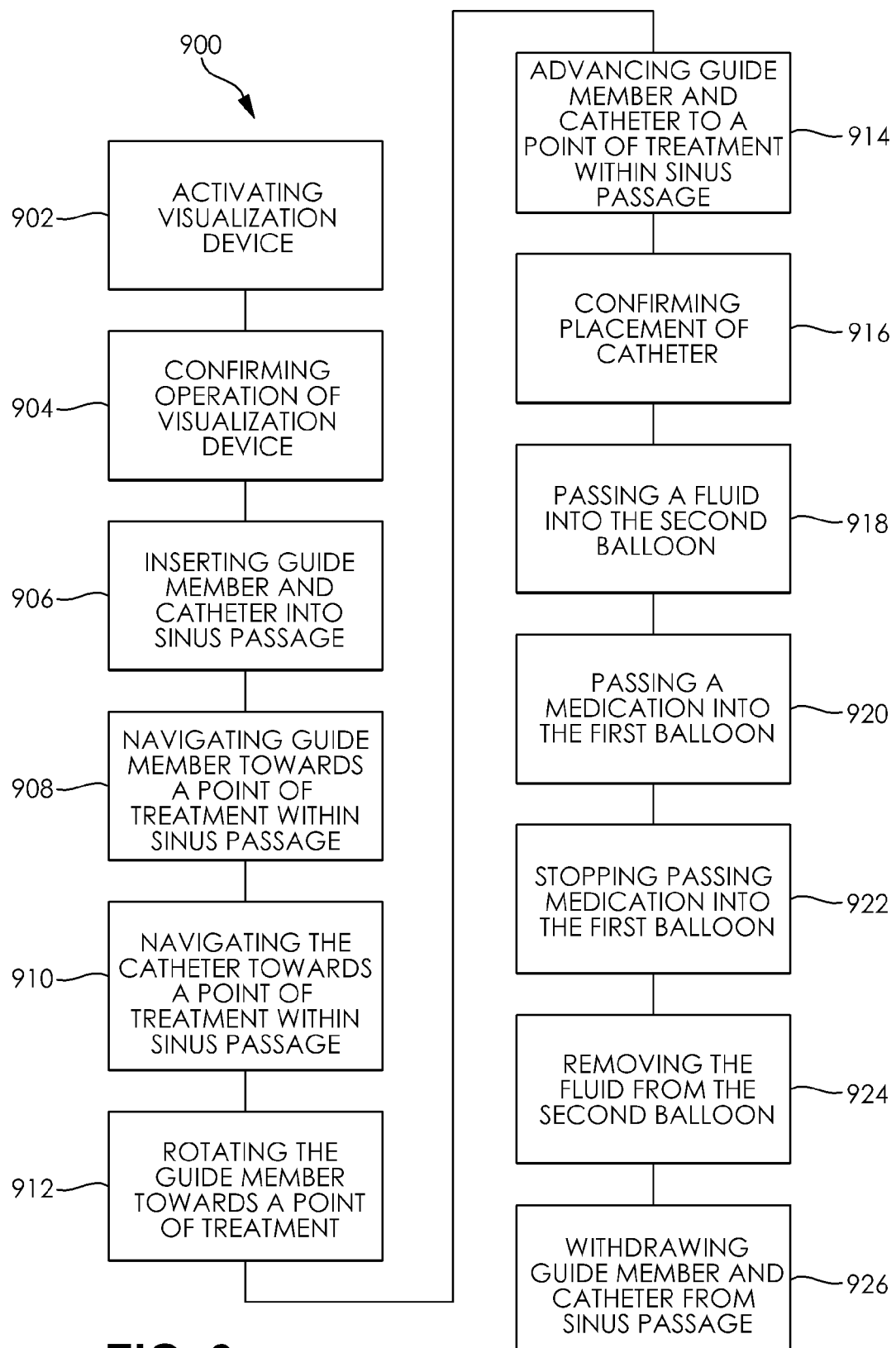
FIG. 9 is a flowchart representation of another exemplary method of treatment.

FIG. 9 is a flowchart representation of an exemplary method 900 of treating tissue within a sinus passage (e.g., eustachian tube) defined by a passage wall. The method 900 is similar to that described above with respect to method 800, except as described below. An initial step 902 comprises activating a visualization device. Another step 904 comprises confirming operation of the visualization device. Another step 906 comprises inserting a guide member and catheter each having a proximal end and a distal end into a sinus passage such that the distal end of the catheter is disposed in the sinus passage. Another step 908 comprises navigating the distal end of the guide member towards a point of treatment. Another step 910 comprises navigating the distal end of the catheter towards a point of treatment within the sinus passage. Another step 912 comprises rotating the guide member towards a point of treatment. Another step 914 comprises advancing the guide member and catheter to a point of treatment. Another step 916 comprises confirming placement of the catheter. Another step 918 comprises passing a fluid through the inflation lumen and into the second balloon with a pressure sufficient to inflate the second balloon and provide contact between a portion of the first balloon and the passage wall. Another step 920 comprises passing a medication through the infusion lumen and into the first balloon with a pressure sufficient to expel the medication through the one or more pores. Another step 922 comprises stopping passing the medication through the infusion lumen. Another step 924 comprises removing the fluid from the second balloon. Another step 926 comprises withdrawing the distal end of the guide member and catheter from the sinus passage.

The step of passing a medication through the infusion lumen and into the first balloon with a pressure sufficient to expel the medication through the one or more pores can be accomplished by passing any suitable fluid, drug, and/or agent through the one or more pores. Examples of medications considered suitable include, but are not limited to, anti-inflammatories (e.g., steroids), antineoplastics (e.g., mitomycin), cytotoxics, adrenaline (e.g., epinephrine), antibiotics, antifungal agents, and/or anti-proliferatives (e.g., such as those used on coronary stents), or a combination thereof.

While various catheter configurations, steps, alternative steps, and optional steps have been described above with respect to treating tissue in a sinus passage, these catheter configurations, steps, alternative steps, and optional steps can be included in, accomplished concurrently with, and/or accomplished in the alternative to, the methodologies, catheter configurations, steps, alternative steps, and/or optional steps described above and/or below with respect to treating tissue in a bodily passage, sinus cavity, and/or airway.

Figure 10:
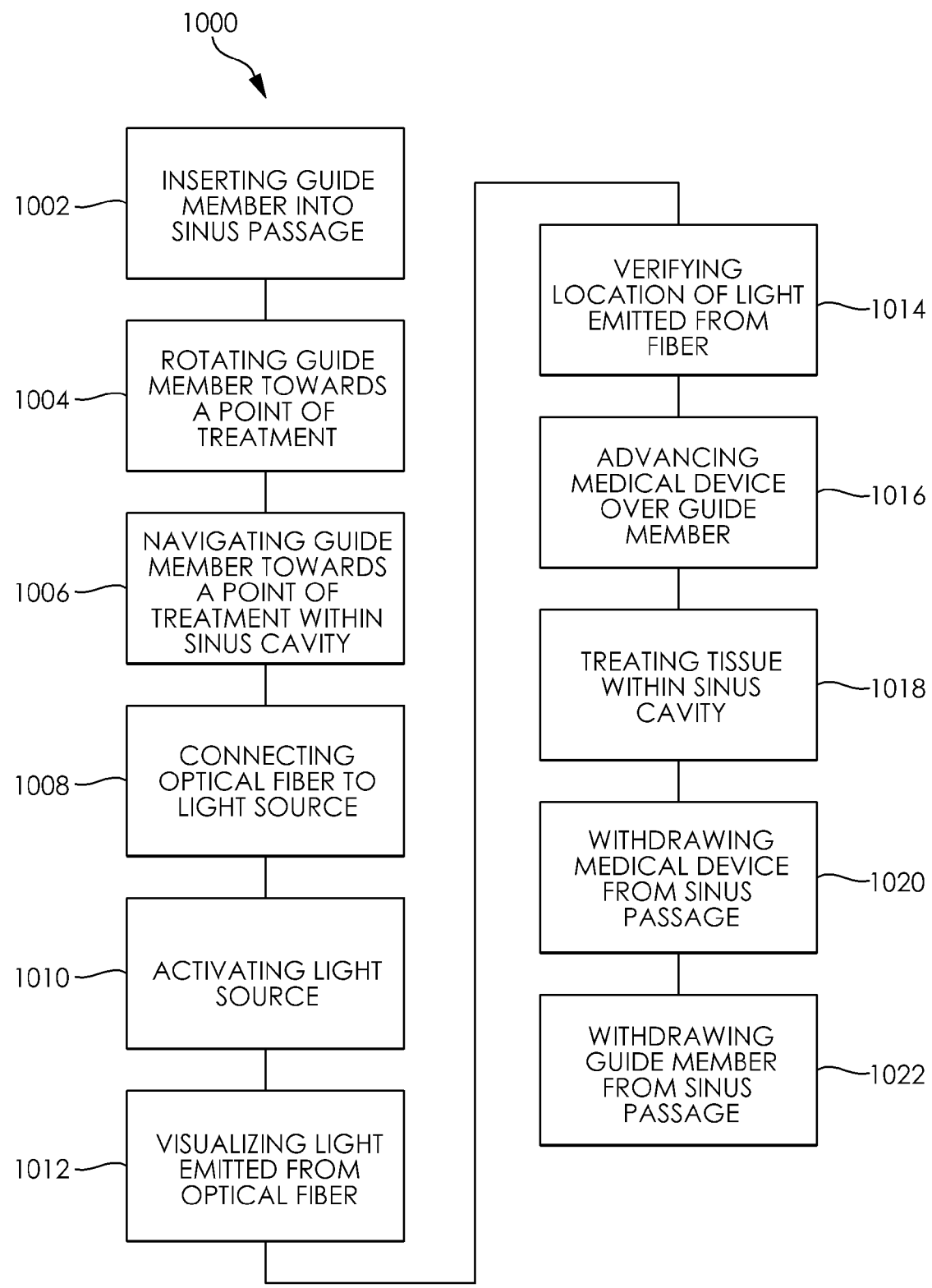
FIG. 10 is a flowchart representation of another exemplary method of treatment.

FIG. 10 is a flowchart representation of an exemplary method 1000 of treating tissue in a sinus passage, defined by a passage wall, in communication with two or more sinus cavities using a light source. Any suitable medical device that defines at least one lumen extending between the proximal end and the distal end can be used to accomplish this method, and skilled artisans will be able to select a suitable medical device according to a particular embodiment based on various considerations, including the intended use of the device. Example devices considered suitable to advance over a length of an elongate tubular member include, but are not limited to, catheters, irrigation catheters, balloon catheters, the catheters described herein (e.g., catheter 200, catheter 300), and any other suitable medical device. In this exemplary method, the guide member omits the inclusion of projection 160 and has a fitting 180 releasably attached to the proximal end 122 of the elongate tubular member 120. Again, any suitable medical device that defines at least one lumen can be used in combination with the guide member.

An initial step 1002 comprises inserting a guide member having a proximal end and a distal end into said sinus passage such that the distal end of the guide member is disposed in the sinus passage. Another step 1004 comprises rotating the guide member towards a point of treatment. Another step 1006 comprises navigating the distal end of the guide member towards a point of treatment within said sinus cavity. Another step 1008 comprises connecting the distal end of the optical fiber to said light source. Another step 1010 comprises activating the said light source such that light emits from the distal end of the optical fiber. Another step 1012 comprises visualizing light being emitted from the optical fiber and passing through an area of skin of said patient. Another step 1014 comprises verifying that the location at which the light passes through the skin of said patient is indicative of the sinus cavity intended to be treated. Another step 1016 comprises advancing a medical device having a proximal end, a distal end, and defining at least one lumen along the path defined by the previously placed guide member into said sinus passage and into the sinus cavity such that the distal end of the medical device is disposed in the sinus cavity. Another step 1018 comprises treating said tissue within the sinus cavity by using the medical device. Another step 1020 comprises withdrawing the distal end of the medical device from the sinus cavity and sinus passage. Another step 1022 comprises withdrawing the distal end of the guide member from the sinus cavity and sinus passage.

By releasably attaching the fitting 180 to the proximal end of the elongate tubular member 120 and omitting the projection 160 a user can advance any suitable medical device over the guide member to perform a procedure. A skilled artisan will be able to select a suitable medical device according to a particular embodiment based on various considerations, including the procedure intended to be performed.

The step of inserting the distal end of a guide member into a sinus passage such that the distal end of the guide member is disposed in the sinus passage can be accomplished by a user locating the sinus passage and advancing the distal end of the guide member into the sinus passage.

The step of rotating the guide member towards a point of treatment can be accomplished by a user rotating the guide member (e.g., fitting 180) in a clockwise or counterclockwise direction around the lengthwise axis of the elongate tubular member. For example, to align the distal end of the coil member with an entrance of a sinus cavity when two or more sinus cavities are present, the user can rotate the guide member (e.g., fitting 180) in a clockwise or counterclockwise direction around the lengthwise axis of the elongate tubular member to properly positioned the distal end of the guide member towards the sinus cavity intended to be treated.

The step of navigating the distal end of the guide member towards a point of treatment within said sinus cavity can be accomplished by a user placing a distal force on any portion of the device to advance the distal end of the guide member into the sinus cavity.

The step of connecting the distal end of the optical fiber to the light source can be accomplished by a user connecting the distal end to the light source using any suitable method of attachment, and skilled artisans will be able to select a suitable method of attachment based on various considerations, including the intended use of the device. An example method considered suitable, includes, but is not limited to, using a fiber coupling.

The step of activating the light source can be accomplished by a user turning on the light source (e.g., power supply) such that the light is emitted from the light source and/or optical fiber.

The step of visualizing light being emitted from the optical fiber and passing through an area of skin of said patient can be accomplished by a user reviewing the patient and locating the light being emitted from the optical fiber transcutaneously.

The step of verifying that the location at which the light passes through the skin of said patient is indicative of the sinus cavity intended to be treated can be treated by the user determining that the light being viewed transcutaneously is indicative of the distal end of the guide member being positioned in the sinus cavity intended to be treated.

The step of advancing a medical device having a proximal end, a distal end, and defining at least one lumen along the path defined by the previously placed guide member into said sinus passage and into the sinus cavity such that the distal end of the medical device is disposed in the sinus cavity can accomplished by removing the fitting of the guide member and inserting the proximal end of the guide member into the at least one lumen defined by the medical device and subsequently sliding the medical device distally over the guide member. An optional step includes reattaching the fitting to the proximal end of the guide member subsequent to the medical device being passed over a length of the guide member.

Alternatively, if the fitting is omitted, the medical device can be advanced over the guide member without removing, or replacing, the fitting on the proximal end of the guide member.

The step of treating said tissue within the sinus cavity by using the medical device can be accomplished using any suitable method of treatment, and skilled artisans will be able to select a suitable method of treatment according to a particular embodiment based on various considerations, including the bodily passage intended to be treated. Example methods of treatment considered suitable include, but are not limited to, those described herein, dilating a stricture, irrigating the sinus cavity, providing suction within the sinus cavity, removing one or more objects, or any other suitable method.

The steps of withdrawing the medical device and guide member from the sinus cavity and sinus passage can be accomplished by the user placing a proximal force on each of the medical device and guide member, in combination or separately, until they are completely removed from the sinus cavity and sinus passage.

While various catheter configurations, steps, alternative steps, and optional steps have been described above with respect to treating tissue in a sinus passage, these catheter configurations, steps, alternative steps, and optional steps can be included in, accomplished concurrently with, and/or accomplished in the alternative to, the methodologies, catheter configurations, steps, alternative steps, and/or optional steps described above with respect to treating tissue in a bodily passage, sinus cavity, airway, and/or sinus passage.

The foregoing detailed description provides exemplary embodiments of the invention and includes the best mode for practicing the invention. The description and illustration of embodiments is intended only to provide examples of the invention, and not to limit the scope of the invention, or its protection, in any manner.

We claim:

1. A medical device adapted to be used with a light source for the identification and treatment of a bodily passage, said medical device comprising:

an elongate tubular member having a first proximal end, a first distal end, a first lengthwise axis, and defining a first lumen extending between the first proximal end and the first distal end;

a coil member having a second proximal end, a second distal end, a second lengthwise axis, and defining a curve and a second lumen, the curve defined along the second lengthwise axis of the coil member and disposed between the second proximal end and the second distal end, the curve directing the second distal end away from the first lengthwise axis of the elongate tubular member, the second lumen extending between the second proximal end and the second distal end, the second proximal end attached to the first distal end of the elongate tubular member;

an optical fiber disposed in the first lumen and the second lumen and having a third proximal end adapted to be operatively connected to said light source, the optical fiber attached to the coil member at a first location proximal to the curve and a second location distal to the curve;

a projection disposed on the elongate tubular member and extending radially outward from the elongate tubular member;

a catheter comprising an elongate main body having a fourth proximal end, a fourth distal end, and defining a third lumen and a recess, the third lumen extending between the fourth proximal end and the fourth distal end, the recess extending from the fourth proximal end into the third lumen toward the fourth distal end, the third lumen having a first diameter and the recess having a second diameter, the second diameter greater than the first diameter; and further comprising a collar disposed on the fourth proximal end, the collar defining a passageway having a third diameter;

wherein the elongate tubular member is disposed within the third lumen such that the projection is disposed within the recess defined by the catheter;

wherein the projection has an outside diameter that is greater than the first diameter and less than the second diameter;

wherein the elongate tubular member is disposed through the passageway; and wherein the outside diameter of the projection is greater than the third diameter of the passageway.

2. The medical device of claim 1, wherein the collar is releasably attached to the fourth proximal end.

3. A medical device adapted to be used with a light source for the identification and treatment of a bodily passage, said medical device comprising:

a catheter comprising an elongate main body having a first proximal end, a first distal end, and defining a first lumen and a recess, the first lumen extending between the first proximal end and the first distal end, the recess extending from the first proximal end into the first lumen toward the first distal end, the first lumen having a first diameter and the recess having a second diameter, the second diameter greater than the first diameter;

an elongate tubular member having a second proximal end, a second distal end, and defining a second lumen extending between the second proximal end and the second distal end;

a coil member having a third proximal end, a third distal end, and defining a curve and a third lumen, the curve disposed between the third proximal end and the third distal end, the third lumen extending between the third proximal end and the third distal end, the third proximal end attached to the second distal end of the elongate tubular member;

an optical fiber disposed in the second lumen and the third lumen and having a fourth proximal end adapted to be operatively connected to said light source, the optical fiber attached to the coil member at a first location proximal to the curve and a second location distal to the curve;

a projection disposed on the elongate tubular member and extending radially outward from the elongate tubular member, the projection having an outside diameter that is greater than the first diameter and less than the second diameter; and further comprising a collar disposed on the first proximal end, the collar defining a passageway having a third diameter;

wherein the elongate tubular member is disposed within the first lumen such that the projection is disposed within the recess defined by the catheter;

wherein the elongate tubular member is disposed through the passageway;

wherein the outside diameter of the projection is greater than the third diameter of the passageway; and wherein the collar is releasably attached to the fourth proximal end.

4. A medical device adapted to be used with a light source for the identification and treatment of a bodily passage, said medical device comprising:

a catheter comprising an elongate main body having a first proximal end, a first distal end, and defining a first lumen and a recess, the first lumen extending between the first proximal end and the first distal end, the recess extending from the first proximal end into the first lumen toward the first distal end, the first lumen having a first diameter and the recess having a second diameter, the second diameter greater than the first diameter;

an elongate tubular member having a second proximal end, a second distal end, and defining a second lumen extending between the second proximal end and the second distal end;

a coil member having a third proximal end, a third distal end, and defining a curve and a third lumen, the curve disposed between the third proximal end and the third distal end, the third lumen extending between the third proximal end and the third distal end, the third proximal end attached to the second distal end of the elongate tubular member;

an optical fiber disposed in the second lumen and the third lumen and having a fourth proximal end adapted to be operatively connected to said light source, the optical fiber attached to the coil member at a first location proximal to the curve and a second location distal to the curve;

a projection disposed on the elongate tubular member and extending radially outward from the elongate tubular member, the projection having an outside diameter that is greater than the first diameter and less than the second diameter; and a collar disposed on the first proximal end, the collar defining a passageway having a third diameter;

wherein the elongate tubular member is disposed within the first lumen such that the projection is disposed within the recess defined by the catheter;

wherein the elongate tubular member is disposed through the passageway; and wherein the outside diameter of the projection is greater than the third diameter of the passageway.

* * * * *